(12) United States Patent
Mason et al.

(10) Patent No.: US 12,297,443 B2
(45) Date of Patent: *May 13, 2025

(54) OPTIMIZED PLANT EXPRESSION SYSTEMS

(71) Applicant: ARIZONA BOARD OF REGENTS ON BEHALF OF ARIZONA STATE UNIVERSITY, Scottsdale, AZ (US)

(72) Inventors: Hugh Mason, Phoenix, AZ (US); Mary Pardhe, Phoenix, AZ (US); Andrew Diamos, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 933 days.

This patent is subject to a terminal disclaimer.

(21) Appl. No.: 17/190,745

(22) Filed: Mar. 3, 2021

(65) Prior Publication Data
US 2021/0198693 A1  Jul. 1, 2021

Related U.S. Application Data

(63) Continuation-in-part of application No. 17/073,102, filed on Oct. 16, 2020, now abandoned, and a continuation-in-part of application No. 16/976,739, filed as application No. PCT/US2019/020621 on Mar. 4, 2019.

(60) Provisional application No. 62/984,491, filed on Mar. 3, 2020, provisional application No. 62/916,211, filed on Oct. 16, 2019, provisional application No. 62/638,010, filed on Mar. 2, 2018.

(51) Int. Cl.
*C12N 15/86* (2006.01)
*C12N 15/82* (2006.01)

(52) U.S. Cl.
CPC ......... *C12N 15/86* (2013.01); *C12N 15/8205* (2013.01); *C12N 15/8258* (2013.01); *C12N 2750/12043* (2013.01)

(58) Field of Classification Search
None
See application file for complete search history.

(56) References Cited

U.S. PATENT DOCUMENTS

| | | | |
|---|---|---|---|
| 7,026,123 B1 | 4/2006 | Duvick | |
| 9,506,079 B2 * | 11/2016 | Mason | C12N 15/8203 |
| 10,125,373 B2 * | 11/2018 | Mason | C07K 16/2887 |
| 2003/0079248 A1 * | 4/2003 | Mason | C12N 15/8203 |
| | | | 435/235.1 |
| 2014/0130205 A1 | 5/2014 | Bhyri | |
| 2015/0368660 A1 | 12/2015 | Mason | |
| 2017/0081676 A1 | 3/2017 | Gupta | |

OTHER PUBLICATIONS

Beyene et al., "Unprecedented enhancement of transient gene expression from minimal cassettes using a double terminator", Plant Cell Rep, (Oct. 22, 2010), vol. 30, doi:doi:10.1007/s00299-010-0936-3, pp. 13-25, XP019869854.
Diamos et al., "5' and 3' Untranslated Regions Strongly Enhance Performance of Geminiviral Replicons in Nicotiana benthamiana Leaves", Front Plant Sci, (Feb. 24, 2016), vol. 7, No. 200, pp. 1-15.
Diamos et al., "Chimeric 3' flanking regions strongly enhance gene expression in plants", Plant Biotechnol J, (May 21, 2018), vol. 16, pp. 1971-1982.
Diamos, A.G., "Chimeric 3' flanking regions strongly enhance gene expression in plants", Optimization of a Viral System to Produce Vaccines and other Biopharmaceuticals in Plants, Doctoral Thesis, (Dec. 31, 2017), pp. 86-132, URL: https://repository.asu.edu/attachments/194162/content/Diamos_asu_0010E_17585.pdf, (May 20, 2019).
Diamos, Andy (Doctoral Dissertation on Optimization of a Viral System to Produce Vaccines and Other Biophrmaceuticals in plants, Dec. 2017) (Year: 2017).
Halweg, C. et al., "The Rb7 Matrix Attachment Region Increases the Likelihood and Magnitude of Transgene Expression in Tobacco Cells: A Flow Cytometric Study", The Plant Cell, Feb. 2005, vol. 17, No. 2, pp. 418-429 <DOI:10.1105/tpc.104.028100>.
Ji et al., "TM6, a novel nuclear matrix attachment region, enhances its flanking gene expression through influencing their chromatin structure", Mol Cells, (Jul. 12, 2013), vol. 36, doi:doi:10.1007/s10059-013-0092-z, pp. 127-137, XP055354122.
Rosenthal et al., "An intronless form of the tobacco extensin gene terminator strongly enhances transient gene expression in plant leaves", Plant Mol Biol, (Feb. 10, 2018), vol. 96, pp. 429-443.

(Continued)

*Primary Examiner* — Medina A Ibrahim
(74) *Attorney, Agent, or Firm* — BOOTH UDALL FULLER, PLC; Rodney J. Fuller

(57) ABSTRACT

Improved plant transient expression systems using optimized geminiviral vectors that efficiently produce heteromultimeric proteins are described herein. Examples of high yields are shown herein, including two, three, or four fluorescent proteins coexpressed simultaneously. Various antibodies were produced using the optimized vectors with special focus given to the creation and production of a chimeric broadly neutralizing anti-flavivirus antibody. The variable regions of this murine antibody, 2A10G6, were codon optimized and fused to a human IgG1. Analysis of the chimeric antibody showed that it was efficiently expressed in plants, can be purified to near homogeneity by a simple one-step purification process, retains its ability to recognize the Zika virus envelope protein, and induce an immune response against Zika virus. Two other monoclonal antibodies were produced at similar levels. This technology is versatile tool for the production of a wide spectrum of pharmaceutical multi-protein complexes in a fast, powerful, and cost-effective way.

7 Claims, 10 Drawing Sheets
(10 of 10 Drawing Sheet(s) Filed in Color)
Specification includes a Sequence Listing.

(56) References Cited

OTHER PUBLICATIONS

Stewart et al "Non-optimal TATA Elements Exhibit Diverse Mechanistic Consequences", (JBC, 2006, 281(32): 22665-22673) (Year: 2006).

* cited by examiner

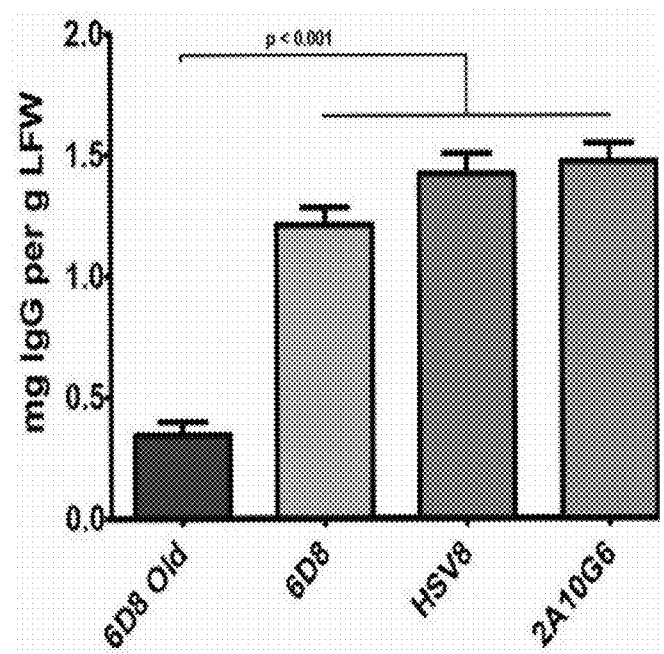
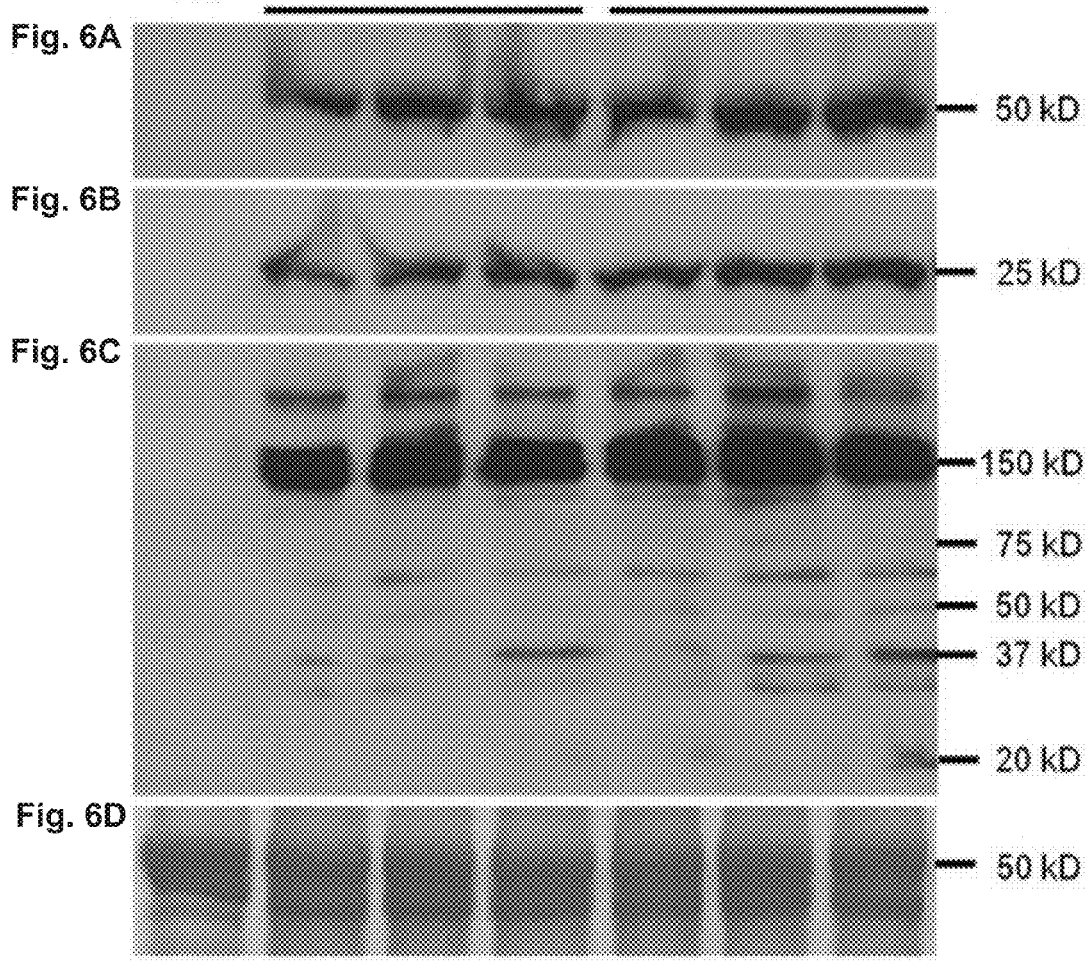

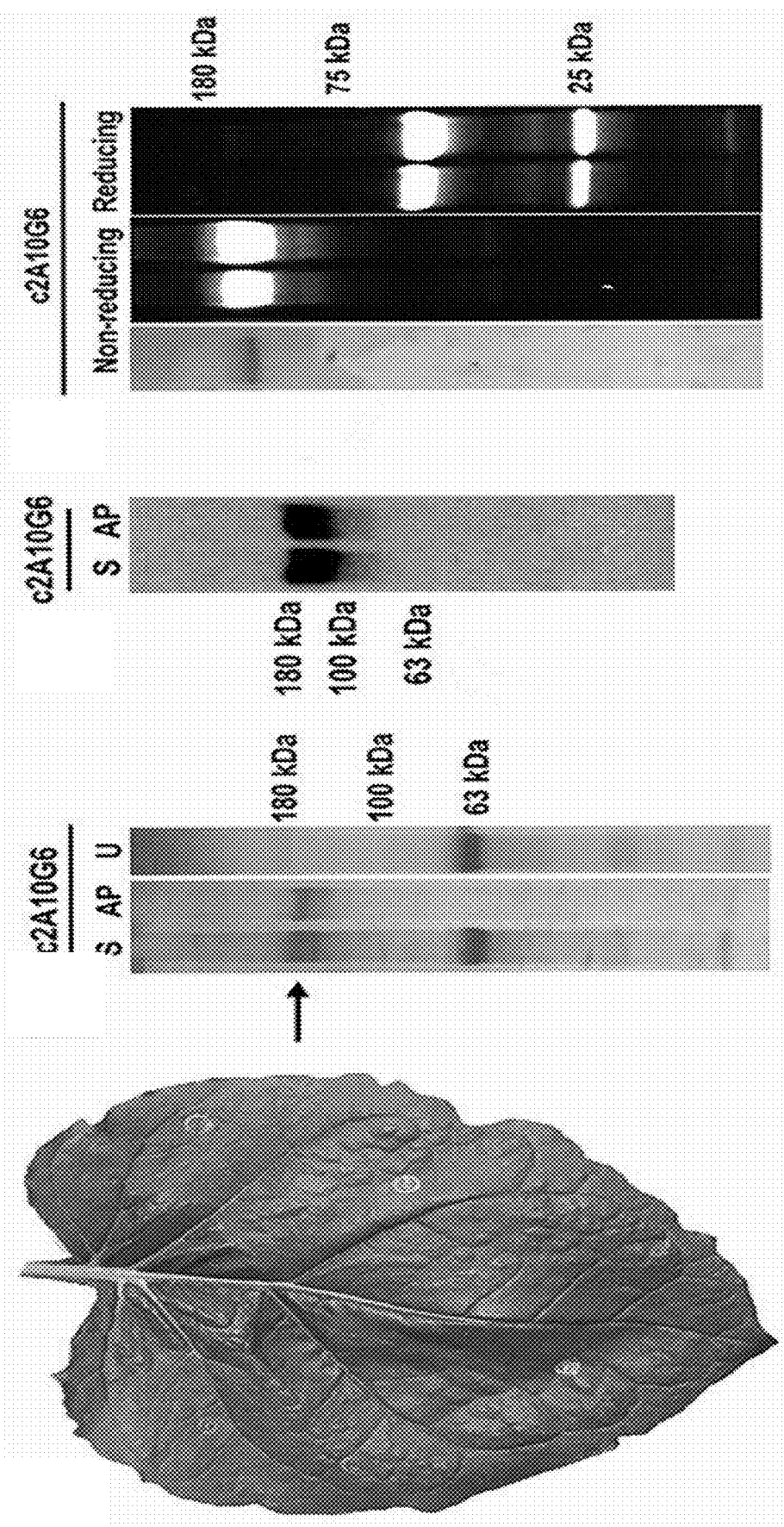

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
```
gcggtaccca attcgcccta tagtgagtcg                              30

<210> SEQ ID NO 2
<211> LENGTH: 56
<212> TYPE: DNA
<213> ORGANISM: Artificial Sequence
<220> FEATURE:
<223> OTHER INFORMATION: Primer

<400> SEQUENCE: 2
gtgtcgtgct ccaccatgcc gtcgacgcac tagtcgatag cttgatgcat gttgtc    56

<210> SEQ ID NO 3
<211> LENGTH: 56
<212> TYPE: DNA
<213> ORGANISM: Artificial Sequence
<220> FEATURE:
<223> OTHER INFORMATION: Primer

<400> SEQUENCE: 3
gacaacatgc atcaagctat cgactagtgc gtcgacggca tggtggagca cgacac    56

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gagagctcca ccgcggtggc                                         20

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
ggactagtga ccctcctgca ggtcaac                                 27

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gcgtcgaccg aaactgaaca aaacatacac                              30

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
ggggtctctc gtggtgccga ggtcactaga c                            31

<210> SEQ ID NO 8
<211> LENGTH: 19
<212> TYPE: DNA
<213> ORGANISM: Artificial Sequence

```
<220> FEATURE:
<223> OTHER INFORMATION: Primer

<400> SEQUENCE: 8
ggaaacagct atgaccatg                                            19

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
aatcccacta tccttcgc                                             18

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gcggtctcca ccagaagcaa gagaagc                                   27

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
aggggtctcg tggtatggtg agcaagggcg a                              31

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
gcgttaatta aaccaccatg gtgagcaagg gcgaggagc                      39

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gcgtcgaccg aaactgaaca aaacatacac                                30

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ccatctgtct tcatctttcc t                                         21
```

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
caatttgctt tgcattcttg ac                                              22

<210> SEQ ID NO 16
<211> LENGTH: 17111
<212> TYPE: DNA
<213> ORGANISM: Artificial Sequence
<220> FEATURE:
<223> OTHER INFORMATION: pBY11HA-GFP

<400> SEQUENCE: 16
cgatcggtcg attcatagaa gattagattt ttcatagtat tttttaaag taaaccttta       60 actacggtta ggacactttt aagttaaatt taatttgaac ccttaaatta attttaaaa      120 tagataaata tcaatcatcc tgatatgctt ttgaaaaaat gaatgagaaa gatgattcaa     180
ttaaggccac attttaatca tgactaaaat aatatacagt ataatttcat atatatttgc     240
tttaaaaaaa aattgacaat ccattcgttt ctagcaataa atttcttcaa ccacaaatat     300
attaaagata actacggcat agaaacaaaa atctatgaag aattttgta tacttctat      360 gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600 cttttttgcac tatccccccaa taattagcaa acacaccta gactagattt gttttgctaa   660
cccaattgat attaattata tatgattaat atttatatgt atatgaatt ggttaataaa     720 atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga accgaatac    1140 tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtggggtc catctttggg accactgtcg gcagaggcat   1740

```
cttcaacgat ggcctttcct ttatcgcaat gatggcattt gtaggagcca ccttcctttt    1800
ccactatctt cacaataaag tgacagatag ctgggcaatg gaatccgagg aggtttccgg    1860
atattaccct ttgttgaaaa gtctcaattg cccttttggtc ttctgagact gtatctttga   1920 tattttttgga gtagacaagt gtgtcgtgct ccaccatgtt ctggcaattc cggttcgctt   1980
gctgtccata aaaccgccca gtctagctat cgccatgtaa gcccactgca agctacctgc    2040
tttctctttg cgcttgcgtt ttccctttgtc cagatagccc agtagctgac attcatccgg   2100
ggtcagcacc gtttctgcgg actggctttc tacgtgttcc gcttccttta gcagcccttg    2160
cgccctgagt gcttgcggca gcgtgaagct ggcgcgccgc tctagcagaa ggcatgttgt    2220
tgtgactccg agggggttgcc tcaaactcta tcttataacc ggcgtggagg catggaggca    2280
agggcatttt ggtaatttaa gtagttagtg gaaaatgacg tcatttactt aaagacgaag    2340
tcttgcgaca agggggggccc acgccgaatt ttaatattac cggcgtggcc ccaccttatc    2400
gcgagtgctt tagcacgagc ggtccagatt taaagtagaa aagttcccgc ccactagggt    2460
taaaggtgtt cacactataa aagcatatac gatgtgatgg tatttgatgg agcgtatatt    2520
gtatcaggta tttccgtcgg atacgaatta ttcgtacgac cctcctgcag gtcaacatgg    2580
tggagcacga cacacttgtc tactccaaaa atatcaaaga tacagtctca gaagaccaaa    2640
gggcaattga actttttcaa caaagggtaa tatccggaaa cctcctcgga ttccattgcc    2700
cagctatctg tcactttatt gtgaagatag tggaaaagga aggtggctcc tacaaatgcc    2760
atcattgcga taaaggaaag gccatcgttg aagatgcctc tgccgacagt ggtcccaaag    2820
atggaccccc acccacgagg agcatcgtgg aaaaagaaga cgttccaacc acgtcttcaa    2880
agcaagtgga ttgatgtgat aacatggtgg agcacgacac acttgtctac tccaaaaata    2940
tcaaagatac agtctcagaa gaccaaaggg caattgagac ttttcaacaa agggtaatat    3000
ccggaaacct cctcggattc cattgcccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg accccacc cacgaggagc atcgtggaaa     3180
aagaagacgt tccaaccacg tcttcaaagc aagtggattg atgtgatatc tccactgacg    3240
taagggatga cgcacaatcc cactatcctt cgcaagaccc ttcctctata taaggaagtt    3300
catttcattt ggagaggacc tcgagaaaca acaaaatca acaaatatag aaaataacgc     3360
atttccaatt ctttgaaatt tctgcaacat ctagcgagac caacaacggt ctctagctaa    3420
agcagaatgc tgagctaaaa gaaaggcttt ttccattttc gagagacaat gagaaaagaa    3480
gaagaagaag aagaagaaga agaagaagaa aagagtaaat aataaagccc cacaggaggc    3540
gaagttcttg tagctccatg ttatctaagt tattgatatt gtttgcccta tattttattt    3600
ctgtcattgt gtatgttttg ttcagtttcg atctccttgc aaaatgcaga gattatgaga    3660
tgaataaact aagttatatt attatacgtg ttaatattct cctcctctct ctagctagcc    3720
ttttgttttc tctttttctt atttgatttt ctttaaatca atccatttta ggagagggcc    3780
agggagtgat ccagcaaaac atgaagatta gaagaaactt ccctctttt tttcctgaaa     3840 acaatttaac gtcgagattt atctcttttt gtaatggaat catttctaca gttatgacgg    3900
ctcactgagg aaatatatag acaaattaag tttggttcta tgagttctaa tttggactta    3960
agagttgttt gaaattctat tttatagtga tgcttataat gtatttggac tgttttctgc    4020
tgtgtgtaag accttttggt ctgtgaactg gaaacataca tgaataaatt tctttgaatt    4080
```

```
tactggaatt tttgcatcaa caaaagaaaa attgaagtta ctaacttgta aatggaacaa    4140
ttgtaatgtt aaaggatata aatatcttaa tatagtgcga tacgaatcac acgaatgcaa    4200
gactttctct ctctgctccc gctcatgctc tcggtgcatg ttagctaaat atacatcggt    4260
gcatccatgg caggagcatg aggacgggga tgaggaaggg agtgaggagg gccaaaagaa    4320
gtacacatag tttcctttgg gagcgaattc tcgattaaaa atcccaatta tatttggtct    4380
aatttagttt ggtattgagt aaaacaaatt cgaaccaaac caaatataaa atatatagtt    4440
tttatatata tgcctttaag acttttata gaattttctt taaaaaatat ctaggtacat    4500
caacgaaaaa ttagtcaaac gactaaaata aataaatatc atgtgttatt aagaaaattc    4560
tcctataaga atatttaat agatcatatg tttgtaaaaa aaattaattt ttactaacac    4620
atatatttac ttatcaaaaa tttgacaaag taagattaaa ataatattca tctaacaaaa    4680
aaaaaaccag aaaatgctga aaacccggca aaaccgaacc aatccaaacc gatatagttg    4740
gtttggtttg atttttgatat aaaccgaacc aactcggtcc atttgcaccc ctaatcataa    4800
tagcttaat atttcaagat attattaagt taacgttgtc aatatcctgg aaattttgca    4860
aaatgaatca agcctatatg ctgtaatat gaatttaaaa gcagctcgat gtggtggtaa    4920
tatgtaattt acttgattct aaaaaaatat cccaagtatt aataatttct gctaggaaga    4980
aggttagcta cgatttacag caaagccaga atacaaagaa ccataaagtg attgaagctc    5040
gaaatatacg aaggaacaaa tatttttaaa aaaatacgca atgacttgga acaaaagaaa    5100
gtgatatatt ttttgttctt aaacaagcat cccctctaaa gaatggcagt tttcctttgc    5160
atgtaactat tatgctccct tcgttacaaa aattttggac tactattggg aacttcttct    5220
gaaaatagtg gtaccgagtg tacttcaagt cagttggaaa tcataaaat gattatttta    5280
tgaatatatt tcattgtgca agtagataga aattacatat gttacataac acacgaaata    5340
aacaaaaaaa cacaatccaa aacaaacacc ccaaacaaaa taacactata tatatcctcg    5400
tatgaggaga ggcacgttca gtgactcgac gattcccgag caaaaaagt ctccccgtca    5460
cacatatagt gggtgacgca attatcttca aagtaatcct tctgttgact tgtcattgat    5520
aacatccagt cttcgtcagg attccaaaga attatagaag ggatcggtca acatggtgga    5580
gcacgacaca cttgtctact ccaaaaatat caaagataca gtctcagaag accaaagggc    5640
aattgagact tttcaacaaa gggtaatatc cggaaacctc ctcggattcc attgcccagc    5700
tatctgtcac tttattgtga agatagtgga aaaggaaggt ggctcctaca aatgccatca    5760
ttgcgataaa ggaaaggcca tcgttgaaga tgcctctgcc gacagtggtc ccaaagatgg    5820
acccccaccc acgaggagca tcgtggaaaa agaagacgtt ccaaccacgt cttcaaagca    5880
agtggattga tgtgataaca tggtggagca cgacacactt gtctactcca aaaatatcaa    5940
agatacagtc tcagaagacc aaagggcaat tgagactttt caacaaaggg taatatccgg    6000
aaacctcctc ggattccatt gcccagctat ctgtcacttt attgtgaaga gtggaaaa    6060
ggaaggtggc tcctacaaat gccatcattg cgataaagga aaggccatcg ttgaagatgc    6120
ctctgccgac agtggtccca agatggacc cccacccacg aggagcatcg tggaaaaaga    6180
agacgttcca accacgtctt caaagcaagt ggattgatgt gatatctcca ctgacgtaag    6240
ggatgacgca caatcccact atccttcgca agacccttcc tctatataag gaagttcatt    6300
tcatttggag aggacctcga gaacaaaca aaatcaacaa atatagaaaa taacgcattt    6360
ccaattcttt gaaatttctg caacatctag aacaatggtg agcaagggcg aggagctgtt    6420
caccggggtg gtgcccatcc tggtcgagct ggacggcgac gtaaacggcc acaagttcag    6480
```

```
cgtgtccggc gagggcgagg gcgatgccac ctacggcaag ctgaccctga agttcatctg   6540
caccaccggc aagctgcccg tgccctggcc caccctcgtg accaccttca gctacggcgt   6600
gcagtgcttc agccgctacc ccgaccacat gaagcagcac gacttcttca gtccgccat    6660 gcccgaaggc tacgtccagg agcgcaccat cttcttcaag gacgacggca actacaagac   6720
ccgcgccgag gtgaagttcg agggcgacac cctggtgaac cgcatcgagc tgaagggcat   6780
cgacttcaag gaggacggca acatcctggg gcacaagctg gagtacaact acaacagcca   6840
caacgtctat atcatggccg acaagcagaa gaacggcatc aaggtgaact tcaagatccg   6900
ccacaacatc gaggacggca gcgtgcagct cgccgaccac taccagcaga caccccccat   6960
cggcgacggc cccgtgctgc tgcccgacaa ccactacctg agcacccagt ccgccctgag   7020
caaagacccc aacgagaagc gcgatcacat ggtcctgctg gagttcgtga ccgccgccgg   7080
gatcactcac ggcatggacg agctgtacaa gtaagagctc aaagcagaat gctgagctaa   7140
aagaaaggct ttttccattt tcgagagaca atgagaaaag aagaagaaga agaagaagaa   7200
gaagaagaag aaaagagtaa ataataaagc cccacaggag gcgaagttct tgtagctcca   7260
tgttatctaa gttattgata ttgtttgccc tatattttat ttctgtcatt gtgtatgttt   7320
tgttcagttt cgatctcctt gcaaaatgca gagattatga gatgaataaa ctaagttata   7380
ttattatacg tgttaatatt ctcctcctct ctctagctag cctttgtttt tctcttttc    7440 ttatttgatt ttcttttaaat caatccattt taggagaggg ccagggagtg atccagcaaa   7500
acatgaagat tagaagaaac ttccctcttt tttttcctga aaacaattta acgtcgagat   7560
ttatctcttt ttgtaatgga atcatttcta cagttatgac gctcatacag cattcccaga   7620
aagagaaaca gaagaaatat acaaactttc attttgagag cagcacctcg tctattgatt   7680
gcagataata tgcttctcat ttgtatttcc ttttgattat ttttgtttct atcccttgt    7740 ttgagtcaat ctcaaatatt cggtcattgt tggtatgaaa aatcaagcag ttcatgttaa   7800
gagtcaattt aaaattaata ttttttatata gagttgtatg tgaaatgatg ttgtgatttg   7860
gtatatatgg ataaagagct tgtcagttca ttttggtctg attttttggg tatccaaata   7920
agaaacacaa aagggatatg tccctctact atcaaatatt agttataagt attcatgtta   7980
tactattcga tattttctac cccaatcgtt acctatttaa aagtatttac ccctccatct   8040
atcaaacccc tggacccagc tttcctatta catgtggctt catcttaagc ccccaaacct   8100
ttttcttatt tttgattttt aaaggctcat cttaaaattt attactcaaa ttaatacctc   8160
ttaataaccc acctcaagga cccagtaatt aaatatccaa ttagctccag taattggggt   8220
tcatattagc tccagtctta aattttaaag gcgatgatcg tattcctcca cttggttcat   8280
ttatactcaa agaatactca atgtctttag tgtttagata acttttttgta aatcatatag   8340 attgttttaa caaaaaacaa ttcaatagta gattttcaca tgaaagttac ataaaaattc   8400
tttaaaatta cttctcaaa aaattgttcc aaacatatta tcccacaatt aaactcaatc    8460 tgttttcga acctaaatc aaaaccaatc caactaccctt atataatata taatcaatac    8520
attgtaaaga actgcatgtt cttttaaatt ttgggggcaa agttattccg tacgttcaca   8580
catgtactaa taggaggtaa taaatgatat gtgaaacaat cgaggtgtaa acaagctagc   8640
atgaattctc gattaaaaat cccaattata tttggtctaa tttagtttgg tattgagtaa   8700
aacaaattcg aaccaaacca aaatataaat atatagtttt tatatatatg cctttaagac   8760
tttttataga attttctta aaaaatatct aggtacatca acgaaaaatt agtcaaacga   8820
```

```
ctaaaataaa taaatatcat gtgttattaa gaaaattctc ctataagaat attttaatag   8880
atcatatgtt tgtaaaaaaa attaatttt actaacacat atatttactt atcaaaaatt    8940
tgacaaagta agattaaaat aatattcatc taacaaaaaa aaaaccagaa aatgctgaaa   9000
acccggcaaa accgaaccaa tccaaaccga tatagttggt ttggtttgat tttgatataa   9060
accgaaccaa ctcggtccat ttgcacccct aatcataata gctttaatat ttcaagatat   9120
tattaagtta acgttgtcaa tatcctggaa attttgcaaa atgaatcaag cctatatggc   9180
tgtaatatga atttaaaagc agctcgatgt ggtggtaata tgtaatttac ttgattctaa   9240
aaaaatatcc caagtattaa taatttctgc taggaagaag gttagctacg atttacagca   9300
aagccagaat acaagaacc ataaagtgat tgaagctcga aatatacgaa ggaacaaata    9360
ttttaaaaa aatacgcaat gacttggaac aaaagaaagt gatatatttt ttgttcttaa    9420
acaagcatcc cctctaaaga atggcagttt tcctttgcat gtaactatta tgctcccttc   9480
gttacaaaaa ttttggacta ctattgggaa cttcttctga aaatagtggt accgagtgta   9540
cttcaagtca gttggaaatc aataaaatga ttattttatg aatatatttc attgtgcaag   9600
tagatagaaa ttacatatgt tacataacac acgaaataaa caaaaaaaca caatccaaaa   9660
caaacacccc aaacaaaata acactatata tatcctcgta tgaggagagg cacgttcagt   9720
gactcgacga ttcccgagca aaaaaagtct ccccgtcaca catatagtgg gtgacgcaat   9780
tatcttcaaa gtaatccttc tgttgacttg tcattgataa catccagtct tcgtcaggat   9840
tgcaaagaat tatagaaggg attccacctt ttattttctt cttttttcca tatttagggt   9900
tgacagtgaa atcagactgg caacctatta attgcttcca caatgggacg aacttgaagg   9960
ggatgtcgtc gatgatatta taggtggcgt gttcatcgta gttggtgaag tcgatggtcc  10020
cgttccagta gttgtgtcgc ccagagacttc tagcccaggt ggtctttccg gtacgagttg  10080
gtccgcagat gtagaggctg gggtgtctga ccccagtcct tccctcatcc tggttagatc  10140
ggccatccac tcaaggtcag attgtgcttg atcgtaggag acaggatgta tgaaagtgta  10200
ggcatcgatg cttacatgat ataggtgcgt ctctctccag ttgtgcagat cttcgtggca  10260
gcggagatct gattctgtga agggcgacac gtactgctca ggttgtggag gaaataattt  10320
gttggctgaa tattccagcc attgaagctt tgttgcccat tcatgaggga actcttcttt  10380
gatcatgtca agatactcct ccttagacgt tgcagtctgg ataatagttc gccatcgtgc  10440
gtcagatttg cgaggagaca ccttatgatc tcggaaatct cctctggttt taatatctcc  10500
gtcctttgat atgtaatcaa ggacttgttt agagtttcta gctggctgga tattagggtg  10560
atttccttca aaatcgaaaa agaaggatc tctaatacaa ggttttttat caagctggat   10620
aagagcatga tagtgggtag tgccatcttg atgaagctca gaagcaacac caaggaagaa  10680
aataagaaaa ggtgtgagtt tctcccagag aaactggaat aaatcatctc tttgagatga  10740
gcacttgggg taggtaagga aaacatattt agattggagt ctgaagttct tgctagcaga  10800
aggcatgttg ttgtgactcc gaggggttgc ctcaaactct atcttataac cggcgtggag  10860
gcatggaggc aagggcattt tggtaattta agtagttagt ggaaaatgac gtcatttact  10920
taaagacgaa gtcttgcgac aagggggggcc cacgccgaat tttaatatta ccggcgtggc  10980
cccaccttat cgcgagtgct ttagcacgag cggtccagat ttaaagtaga aaagttcccg  11040
cccactaggg ttaaaggtgt tcacactata aaagcatata cgatgtgatg gtatttgatg  11100
gagcgtatat tgtatcaggt atttccgtcg gatacgaatt attcgtacgg ccggaccggt  11160
cccctaggcc ggccaattcg agatcggccg cggctgagtg gctccttcaa tcgttgcggt  11220
```

```
tctgtcagtt ccaaacgtaa aacggcttgt cccgcgtcat cggcggggt cataacgtga    11280 ctcccttaat tctccgctca tgatcagatt gtcgtttccc gccttcagtt taaactatca    11340
gtgtttgaca ggatatattg gcgggtaaac ctaagagaaa agagcgttta ttagaataat    11400
cggatattta aaagggcgtg aaaaggttta tccgttcgtc catttgtatg tgcatgccaa    11460
ccacagggtt ccccagatct ggcgccggcc agcgagacga gcaagattgg ccgccgcccg    11520
aaacgatccg acagcgcgcc cagcacaggt gcgcaggcaa attgcaccaa cgcatacagc    11580
gccagcagaa tgccatagtg ggcggtgacg tcgttcgagt gaaccagatc gcgcaggagg    11640
cccggcagca ccggcataat caggccgatg ccgacagcgt cgagcgcgac agtgctcaga    11700
attacgatca ggggtatgtt gggtttcacg tctggcctcc ggagactgtc atacgcgtaa    11760
aaaggccgcg ttgctggcgt ttttccatag gctccgcccc cctgacgagc atcacaaaaa    11820
tcgacgctca agtcagaggt ggcgaaaccc gacaggacta taaagatacc aggcgtttcc    11880
ccctggaagc tccctcgtgc gctctcctgt tccgaccctg ccgcttaccg gatacctgtc    11940
cgcctttctc ccttcgggaa gcgtggcgct ttctcatagc tcacgctgta ggtatctcag    12000
ttcggtgtag tcgttcgct ccaagctggg ctgtgtgcac gaaccccccg ttcagcccga    12060
ccgctgcgcc ttatccggta actatcgtct tgagtccaac ccggtaagac acgacttatc    12120
gccactggca gcagccactg gtaacaggat tagcagagcg aggtatgtag gcggtgctac    12180
agagttcttg aagtggtggc ctaactacgg ctacactaga aggacagtat ttggtatctg    12240
cgctctgctg aagccagtta ccttcggaaa aagagttggt agctcttgat ccggcaaaca    12300
aaccaccgct ggtagcggtg gtttttttgt ttgcaagcag cagattacgc gcagaaaaaa    12360
aggatctcaa gaagatcctt tgatctttc tacgggtct gacgctcagt ggaacgaaaa    12420
ctcacgttaa gggattttgg tcatgagatt atcaaaaagg atcttcacct agatcctttt    12480
aaattaaaaa tgaagtttta atcaatcta aagtatatat gagtaaactt ggtctgcagt    12540
tgccatgttt tacggcagtg agagcagaga tagcgctgat gtccggcggt gcttttgccg    12600
ttacgcacca ccccgtcagt agctgaacag gagggacagc tgatagacac agaagccact    12660
ggagcacctc aaaaacacca tcatacacta aatcagtaag ttggcagcat cacccataat    12720
tgtggtttca aaatcggctc cgtcgatact atgttatacg ccaactttga aaacaacttt    12780
gaaaaagctg ttttctggta tttaaggttt tagaatgcaa ggaacagtga attggagttc    12840
gtcttgttat aattagcttc ttggggtatc tttaaatact gtagaaaaga ggaaggaaat    12900
aataaatggc taaaatgaga atatcaccgg aattgaaaaa actgatcgaa aaataccgct    12960
gcgtaaaaga tacggaagga atgtctcctg ctaaggtata taagctggtg ggagaaaatg    13020
aaaacctata tttaaaaatg acggacagcc ggtataaagg gaccacctat gatgtggaac    13080
gggaaaagga catgatgcta tggctggaag gaaagctgcc tgttccaaag gtcctgcact    13140
ttgaacggca tgatggctgg agcaatctgc tcatgagtga ggccgatggc gtcctttgct    13200
cggaagagta tgaagatgaa caaagccctg aaaagattat cgagctgtat gcggagtgca    13260
tcaggctctt tcactccatc gacatatcgg attgtcccta tacgaatagc ttagacagcc    13320
gcttagccga attggattac ttactgaata acgatctggc cgatgtggat tgcgaaaact    13380
gggaagaaga cactccattt aaagatccgc gcgagctgta tgatttttta aagacggaaa    13440
agcccgaaga ggaacttgtc ttttcccacg cgacctggg agacagcaac atctttgtga    13500
aagatggcaa agtaagtggc tttattgatc ttggagaag cggcagggcg acaagtggt    13560
```

-continued

```
atgacattgc cttctgcgtc cggtcgatca gggaggatat cggggaagaa cagtatgtcg    13620
agctattttt tgacttactg gggatcaagc ctgattggga gaaaataaaa tattatattt    13680
tactggatga attgttttag tacctagatg tggcgcaacg atgccggcga caagcaggag    13740
cgcaccgact tcttccgcat caagtgtttt ggctctcagg ccgaggccca cggcaagtat    13800
ttgggcaagg ggtcgctggt attcgtgcag ggcaagattc ggaataccaa gtacgagaag    13860
gacggccaga cggtctacgg gaccgacttc attgccgata aggtggatta tctggacacc    13920
aaggcaccag gcgggtcaaa tcaggaataa gggcacattg ccccggcgtg agtcggggca    13980
atcccgcaag gagggtgaat gaatcggacg tttgaccgga aggcatacag gcaagaactg    14040
atcgacgcgg ggttttccgc cgaggatgcc gaaaccatcg caagccgcac cgtcatgcgt    14100 gcgcccgcg aaaccttcca gtccgtcggc tcgatggtcc agcaagctac ggccaagatc    14160
gagcgcgaca gcgtgcaact ggctcccccct gccctgcccg cgccatcggc cgccgtggag    14220
cgttcgcgtc gtctcgaaca ggaggcggca ggtttggcga agtcgatgac catcgacacg    14280
cgaggaacta tgacgaccaa gaagcgaaaa accgccggcg aggacctggc aaaacaggtc    14340
agcgaggcca agcaggccgc gttgctgaaa cacacgaagc agcagatcaa ggaaatgcag    14400 cttccttgt tcgatattgc gccgtggccg gacacgatgc gagcgatgcc aaacgacacg    14460
gcccgctctg ccctgttcac cacgcgcaac aagaaaatcc cgcgcgaggc gctgcaaaac    14520
aaggtcattt tccacgtcaa caaggacgtg aagatcacct acaccggcgt cgagctgcgg    14580
gccgacgatg acgaactggt gtggcagcag gtgttggagt acgcgaagcg caccccctatc    14640 ggcgagccga tcaccttcac gttctacgag ctttgccagg acctgggctg gtcgatcaat    14700
ggccggtatt acacgaaggc cgaggaatgc ctgtcgcgcc tacaggcgac ggcgatgggc    14760
ttcacgtccg accgcgttgg gcacctggaa tcggtgtcgc tgctgcaccg cttccgcgtc    14820
ctggaccgtg gcaagaaaac gtcccgttgc caggtcctga tcgacgagga aatcgtcgtg    14880
ctgtttgctg gcgaccacta cacgaaattc atatgggaga agtaccgcaa gctgtcgccg    14940
acggcccgac ggatgttcga ctatttcagc tcgcaccggg agccgtaccc gctcaagctg    15000
gaaaccttcc gcctcatgtg cggatcggat tccacccgcg tgaagaagtg gcgcgagcag    15060
gtcggcgaag cctgcgaaga gttgcgaggc agcggcctgg tggaacacgc ctgggtcaat    15120
gatgacctgt gcattgcaa acgctagggc cttgtggggt cagttccggc tgggggttca    15180
gcagccagcg ctttactggc atttcaggaa caagcgggca ctgctcgacg cacttgcttc    15240
gctcagtatc gctcgggacg cacgcgcgc tctacgaact gccgataaac agaggattaa    15300
aattgacaat tcaatggcaa ggactgccag cgctgccatt tttggggtga ggccgttcgc    15360
ggccgagggg cgcagcccct gggggatgg gaggcccgcg ttagcgggcc gggagggttc    15420
gagaaggggg ggcacccccc ttcggcgtgc gcggtcacgc gcacagggcg cagccctggt    15480
taaaaacaag gtttataaat attggtttaa aagcaggtta aaagacaggt tagcggtggc    15540
cgaaaaacgg gcggaaaccc ttgcaaatgc tggattttct gcctgtggac agcccctcaa    15600
atgtcaatag gtgcgcccct catctgtcag cactctgccc ctcaagtgtc aaggatcgcg    15660
cccctcatct gtcagtagtc gcgccccctca agtgtcaata ccgcagggca cttatcccca    15720
ggcttgtcca catcatctgt gggaaactcg cgtaaaatca ggcgttttcg ccgatttgcg    15780
aggctggcca gctccacgtc gccggccgaa atcgagcctg ccctcatct gtcaacgccg    15840 cgccgggtga tcggccccct caagtgtcaa cgtccgcccc tcatctgtca gtgagggcca    15900
agttttccgc gaggtatcca caacgccggc ggccgcggtg tctcgcacac ggcttcgacg    15960
```

```
gcgtttctgg cgcgtttgca gggccataga cggccgccag cccagcggcg agggcaacca    16020
gcccggtgag cgtcgcaaag gcgctcggtc ttgccttgct cgtcgagatc tggggtcgat    16080
cagccgggga tgcatcaggc cgacagtcgg aacttcgggt ccccgacctg taccattcgg    16140
tgagcaatgg atagggagt tgatatcgtc aacgttcact tctaaagaaa tagcgccact    16200
cagcttcctc agcggcttta tccagcgatt tcctattatg tcggcatagt tctcaagatc    16260
gacagcctgt cacggttaag cgagaaatga ataagaaggc tgataattcg gatctctgcg    16320
agggagatga tatttgatca caggcagcaa cgctctgtca tcgttacaat caacatgcta    16380
ccctccgcga gatcatccgt gtttcaaacc cggcagctta gttgccgttc ttccgaatag    16440
catcggtaac atgagcaaag tctgccgcct acaacggct ctcccgctga cgccgtcccg    16500
gactgatggg ctgcctgtat cgagtggtga ttttgtgccg agctgccggt cggggagctg    16560
ttggctggct ggtggcagga tatattgtgg tgtaaacaaa ttgacgctta gacaacttaa    16620
taacacattg cggacgtttt taatgtactg gggtggtttt tcttttcacc agtgagacgg    16680
gcaacagctg attgcccttc accgcctggc cctgagagag ttgcagcaag cggtccacgc    16740
tggtttgccc cagcaggcga aaatcctgtt tgatggtggt tccgaaatcg gcaaaatccc    16800
ttataaatca aagaatagc ccgagatagg gttgagtgtt gttccagttt ggaacaagag    16860
tccactatta agaacgtgg actccaacgt caaaggcga aaaccgtct atcagggcga    16920 tgcccacta cgtgaaccat cacccaaatc aagttttttg gggtcgaggt gccgtaaagc    16980
actaaatcgg aaccctaaag ggagcccccg atttagagct tgacggggaa agccggcgaa    17040
cgtggcgaga aggaaggga agaaagcgaa aggagcgggc gccattcagg ctgcgcaact    17100
gttgggaagg g                                                        17111

<210> SEQ ID NO 17
<211> LENGTH: 14211
<212> TYPE: DNA
<213> ORGANISM: Artificial Sequence
<220> FEATURE:
<223> OTHER INFORMATION: pBYKEAM-BAGFPas6h

<400> SEQUENCE: 17
cgatcggtcg attcatagaa gattagattt ttcatagtat ttttttaaag taaaccttta      60
actacggtta ggacactttt aagttaaatt taatttgaac ccttaaatta attttttaaaa    120 tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag aatttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaattat    480
ttctctatct atttttcctta tatcatgcat ggtttcacat atatcaaagg ataaaagcaa    540
tctatgtaaa ttatctcact ttattaagtt ttctatctga attattgaga acgtagattt    600 cttttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct cttttctctta ttcagataat tagtaattac acataacaca caactttgat    840
```

```
gcccacatta tagtgattag catgtcacta tgtgtgcatc cttttatttc atacattaat    900
taacttggcc aatccagaag atggacaagt ctagggtcac attgcagggt actctagctt    960
actcgccttc ttttttcgaag gtttgagtac cttcagggca tcctcttgat acattacttt  1020
```
*Note: line 960→1020 transition*
```
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatcccta   1620
cgtcagtgga gatatcacat caatccactt gctttgaaga cgtggttgga acgtcttctt   1680
tttccacgat gctcctcgtg ggtggggtgc catctttggg accactgtcg gcagaggcat   1740
cttcaacgat ggccttttcct ttatcgcaat gatggcattt gtaggagcca ccttccttt   1800
ccactatctt cacaataaag tgacagatag ctgggcaatg gaatccgagg aggtttccgg   1860
atattaccct ttgttgaaaaa gtctcaattg cccttggtc ttctgagact gtatctttga   1920
tattttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg agggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caagggtaa tatccggaaa cctcctcgga ttccattgcc   2700
cagctatctg tcactttatt gtgaagatag tggaaaagga aggtggctcc tacaaatgcc   2760
atcattgcga taaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa gggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gaccccacc cacgaggagc atcgtggaaa   3180
aagaagacgt tccaaccacg tcttcaaagc aagtggattg atgtgatatc tccactgacg   3240
```

```
taagggatga cgcacaatcc cactatcctt cgcaagaccc ttcctctata taaggaagtt    3300
catttcattt ggagaggacc tcgagaaaca aacaaaatca acaaatatag aaaataacgc    3360
atttccaatt ctttgaaatt tctgcaacat ctagaacaat ggctaacaag cacctctcat    3420
tgtctctctt ccttgtgctc cttggtcttt ctgcttctct tgcttctggt atggtgtcca    3480
agggagagga agcttctgga agagccttgt tccagtaccc tatgacttct aaaatcgagt    3540
tgaatggcga gatcaacgga aagaagttta aggttgctgg agagggtttc accccttcat    3600
ctggaagatt caatatgcac gcttactgta ctaccggaga cttgcctatg tcctgggttg    3660
ttatagcttc cccgcttcag tacgggtttc acatgtttgc ccactaccct gaggatatca    3720
ctcacttctt ccaagaatgt tttcctgggt cttatactct cgacagaact ttgaggatgg    3780
agggagacgg tactcttact actcaccacg agtactccct tgaggacggt tgcgttactt    3840
ccaagactac tttgaacgct tctggattcg accccaaggg agccactatg actaagtctt    3900
tcgtcaaaca gctcccaaac gaggtcaaaa tcacccacac cgggccaaat ggtattagac    3960
ttacttccac tgttctctac cttaaggagg acggaactat ccagatcgga actcaagact    4020
gcatcgttac cccagttggc ggcagaaaag ttactcagcc taaggctcac tttcttcata    4080
ctcagatcat tcagaagaag gacccaaacg acaccagaga tcacatcgtt cagactgagc    4140
ttgccgttgc tggaaatctt tggcacggca tggatgagct ttacaagact agtcaccatc    4200
accatcacca ttaagagctc aaagcagaat gctgagctaa agaaaggct tttccatttt    4260 tcgagagaca atgagaaaag aagaagaaga agaagaagaa gaagaagaag aaaagagtaa    4320
ataataaagc cccacaggag gcgaagttct tgtagctcca tgttatctaa gttattgata    4380
ttgtttgccc tatattttat ttctgtcatt gtgtatgttt tgttcagttt cgatctcctt    4440
gcaaaatgca gagattatga gatgaataaa ctaagttata ttattatacg tgttaatatt    4500
ctcctcctct ctctagctag cctttttgttt tctcttttc ttatttgatt ttctttaaat    4560
caatccattt taggagaggg ccagggagtg atccagcaaa acatgaagat tagaagaaac    4620
ttccctcttt ttttttcctga aaacaattta acgtcgagat ttatctcttt ttgtaatgga    4680
atcatttcta cagttatgac gctcatacag cattcccaga aagagaaaca gaagaaatat    4740
acaaactttc attttgagag cagcacctcg tctattgatt gcagataata tgcttctcat    4800
ttgtatttcc ttttgattat ttttgtttct atcccctttgt ttgagtcaat ctcaaatatt    4860
cggtcattgt tggtatgaaa atcaagcag ttcatgttaa gagtcaattt aaaattaata    4920 ttttatata gagttgtatg tgaaatgatg ttgtgatttg gtatatatgg ataaagagct    4980
tgtcagttca ttttggtctg attttttgg tatccaaata agaaacacaa aagggatatg    5040
tccctctact atcaaatatt agttataagt attcatgtta tactattcga tattttctac    5100
cccaatcgtt acctatttaa aagtatttac ccctccatct atcaaacccc tggacccagc    5160
tttcctatta catgtggctt catcttaagc ccccaaacct ttttcttatt tttgattttt    5220
aaaggctcat cttaaaattt attactcaaa ttaatacctc ttaataaccc acctcaagga    5280
cccagtaatt aaatatccaa ttagctccag taattggggt tcatattagc tccagtctta    5340
aattttaaag gcgatgatcg tattcctcca cttggttcat ttatactcaa agaatactca    5400
atgtctttag tgtttagata acttttttgta aatcatatag attgttttaa caaaaaacaa    5460
ttcaatagta gattttcaca tgaaagttac ataaaaattc tttaaaatta ctttctcaaa    5520
aaattgttcc aaacatatta tcccacaatt aaactcaatc tgttttttcga aacctaaatc    5580
```

```
aaaaccaatc caactacctt atataatata taatcaatac attgtaaaga actgcatgtt    5640
cttttaaatt ttgggggcaa agttattccg tacgttcaca catgtactaa taggaggtaa    5700
taaatgatat gtgaaacaat cgaggtgtaa acaagctagc atgaattctc gattaaaaat    5760
cccaattata tttggtctaa tttagtttgg tattgagtaa aacaaattcg aaccaaacca    5820
aaatataaat atatagtttt tatatatatg cctttaagac ttttttataga attttcttta    5880 aaaaatatct aggtacatca acgaaaaatt agtcaaacga ctaaaataaa taaatatcat    5940
gtgttattaa gaaaattctc ctataagaat atttttaatag atcatatgtt tgtaaaaaaa    6000 attaatttt actaacacat atatttactt atcaaaaatt tgacaaagta agattaaaat    6060
aatattcatc taacaaaaaa aaaaccagaa aatgctgaaa acccggcaaa accgaaccaa    6120
tccaaaccga tatagttggt ttggtttgat tttgatataa accgaaccaa ctcggtccat    6180
ttgcacccct aatcataata gctttaatat ttcaagatat tattaagtta acgttgtcaa    6240
tatcctggaa attttgcaaa atgaatcaag cctatatggc tgtaatatga atttaaaagc    6300
agctcgatgt ggtggtaata tgtaatttac ttgattctaa aaaaatatcc caagtattaa    6360
taatttctgc taggaagaag gttagctacg atttacagca aagccagaat acaaagaacc    6420
ataaagtgat tgaagctcga aatatacgaa ggaacaaata tttttaaaaa aatacgcaat    6480
gacttggaac aaaagaaagt gatatatttt ttgttcttaa acaagcatcc cctctaaaga    6540
atggcagttt tccttttgcat gtaactatta tgctcccttc gttacaaaaa ttttggacta    6600
ctattgggaa cttcttctga aaatagtggt accgagtgta cttcaagtca gttggaaatc    6660
aataaaatga ttatttttatg aatatatttc attgtgcaag tagatagaaa ttacatatgt    6720
tacataacac acgaaataaa caaaaaaaca caatccaaaa caaacacccc aaacaaaata    6780
acactatata tatcctcgta tgaggagagg cacgttcagt gactcgacga ttcccgagca    6840 aaaaagtct ccccgtcaca catatagtgg gtgacgcaat tatcttcaaa gtaatccttc    6900
tgttgacttg tcattgataa catccagtct tcgtcaggat tgcaaagaat tatagaaggg    6960
attccacctt ttattttctt ctttttttcca tatttagggt tgacagtgaa atcagactgg    7020
caacctatta attgcttcca caatgggacg aacttgaagg ggatgtcgtc gatgatatta    7080
taggtggcgt gttcatcgta gttggtgaag tcgatggtcc cgttccagta gttgtgtcgc    7140
ccgagacttc tagcccaggt ggtctttccg gtacgagttg gtccgcagat gtagaggctg    7200
gggtgtctga ccccagtcct tccctcatcc tggttagatc ggccatccac tcaaggtcag    7260
attgtgcttg atcgtaggag acaggatgta tgaaagtgta ggcatcgatg cttacatgat    7320
ataggtgcgt ctctctccag ttgtgcagat cttcgtggca gcggagatct gattctgtga    7380
agggcgacac gtactgctca ggttgtggag gaaataattt gttggctgaa tattccagcc    7440
attgaagctt tgttgcccat tcatgaggga actcttcttt gatcatgtca agatactcct    7500
ccttagacgt tgcagtctgg ataatagttc gccatcgtgc gtcagatttg cgaggagaca    7560
ccttatgatc tcggaaatct cctctggttt taatatctcc gtcctttgat atgtaatcaa    7620
ggacttgttt agagtttcta gctggctgga tattagggtg atttccttca aaatcgaaaa    7680
aagaaggatc tctaatacaa ggtttttttat caagctggat aagagcatga tagtgggtag    7740
tgccatcttg atgaagctca gaagcaacac caaggaagaa aataagaaaa ggtgtgagtt    7800
tctcccagag aaactggaat aaatcatctc tttgagatga gcacttgggg taggtaagga    7860
aaacatattt agattggagt ctgaagttct tgctagcaga aggcatgttg ttgtgactcc    7920 gagggggttgc ctcaaactct atcttataac cggcgtggag gcatggaggc aagggcattt    7980
```

```
tggtaattta agtagttagt ggaaaatgac gtcatttact taaagacgaa gtcttgcgac    8040
aaggggggcc cacgccgaat tttaatatta ccggcgtggc cccaccttat cgcgagtgct    8100
ttagcacgag cggtccagat ttaaagtaga aaagttcccg cccactaggg ttaaaggtgt    8160
tcacactata aaagcatata cgatgtgatg gtatttgatg gagcgtatat tgtatcaggt    8220
atttccgtcg gatacgaatt attcgtacgg ccggaccggt cccctaggcc ggccaattcg    8280
agatcggccg cggctgagtg gctccttcaa tcgttgcggt tctgtcagtt ccaaacgtaa    8340
aacggcttgt cccgcgtcat cggcgggggt cataacgtga ctcccttaat tctccgctca    8400
tgatcagatt gtcgtttccc gccttcagtt taaactatca gtgtttgaca ggatatattg    8460
gcgggtaaac ctaagagaaa agagcgttta ttagaataat cggatattta aagggcgtg     8520 aaaaggttta tccgttcgtc catttgtatg tgcatgccaa ccacagggtt ccccagatct    8580
ggcgccggcc agcgagacga gcaagattgg ccgccgcccg aaacgatccg acagcgcgcc    8640
cagcacaggt gcgcaggcaa attgcaccaa cgcatacagc gccagcagaa tgccatagtg    8700
ggcggtgacg tcgttcgagt gaaccagatc gcgcaggagg cccggcagca ccggcataat    8760
caggccgatg ccgacagcgt cgagcgcgac agtgctcaga attacgatca ggggtatgtt    8820
gggtttcacg tctggcctcc ggagactgtc atacgcgtaa aaaggccgcg ttgctggcgt    8880
ttttccatag gctccgcccc cctgacgagc atcacaaaaa tcgacgctca agtcagaggt    8940
ggcgaaaccc gacaggacta taaagatacc aggcgtttcc ccctggaagc tccctcgtgc    9000
gctctcctgt tccgaccctg ccgcttaccg gatacctgtc cgcctttctc ccttcgggaa    9060
gcgtggcgct ttctcatagc tcacgctgta ggtatctcag ttcggtgtag tcgttcgct    9120 ccaagctggg ctgtgtgcac gaaccccccg ttcagcccga ccgctgcgcc ttatccggta    9180
actatcgtct tgagtccaac ccggtaagac acgacttatc gccactggca gcagccactg    9240
gtaacaggat tagcagagcg aggtatgtag gcggtgctac agagttcttg aagtggtggc    9300
ctaactacgg ctacactaga aggacagtat ttggtatctg cgctctgctg aagccagtta    9360
ccttcggaaa aagagttggt agctcttgat ccggcaaaca aaccaccgct ggtagcggtg    9420
gtttttttgt ttgcaagcag cagattacgc gcagaaaaaa aggatctcaa gaagatcctt    9480
tgatcttttc tacggggtct gacgctcagt ggaacgaaaa ctcacgttaa gggattttgg    9540
tcatgagatt atcaaaaagg atcttcacct agatcctttt aaattaaaaa tgaagtttta    9600
aatcaatcta agtatatat gagtaaactt ggtctgcagt tgccatgttt tacggcagtg    9660
agagcagaga tagcgctgat gtccggcggt gcttttgccg ttacgcacca ccccgtcagt    9720
agctgaacag gagggacagc tgatagacac agaagccact ggagcacctc aaaaacacca    9780
tcatacacta aatcagtaag ttggcagcat cacccataat tgtggtttca aaatcggctc    9840
cgtcgatact atgttatacg ccaactttga aaacaacttt gaaaaagctg ttttctggta    9900
tttaaggttt tagaatgcaa ggaacagtga attggagttc gtcttgttat aattagcttc    9960
ttggggtatc tttaaatact gtagaaaaga ggaaggaaat aataaatggc taaaatgaga   10020
atatcaccgg aattgaaaaa actgatcgaa aaataccgct gcgtaaaaga tacggaagga   10080
atgtctcctg ctaaggtata taagctggtg ggagaaaatg aaaacctata tttaaaaatg   10140
acggacagcc ggtataaagg gaccacctat gatgtggaac gggaaaagga catgatgcta   10200
tggctggaag gaaagctgcc tgttccaaag gtcctgcact ttgaacgcca tgatggctgg   10260
agcaatctgc tcatgagtga ggccgatggc gtcctttgct cggaagagta tgaagatgaa   10320
```

-continued

```
caaagccctg aaaagattat cgagctgtat gcggagtgca tcaggctctt tcactccatc    10380
gacatatcgg attgtcccta tacgaatagc ttagacagcc gcttagccga attggattac    10440
ttactgaata acgatctggc cgatgtggat tgcgaaaact gggaagaaga cactccattt    10500
aaagatccgc gcgagctgta tgattttta aagacgaaa agcccgaaga ggaacttgtc      10560
ttttcccacg gcgacctggg agacagcaac atctttgtga aagatggcaa agtaagtggc    10620
tttattgatc ttgggagaag cggcagggcg acaagtggt atgacattgc cttctgcgtc     10680
cggtcgatca gggaggatat cggggaagaa cagtatgtcg agctatttt tgacttactg     10740
gggatcaagc ctgattggga gaaaataaaa tattatattt tactggatga attgttttag    10800
tacctagatg tggcgcaacg atgccggcga caagcaggag cgcaccgact tcttccgcat    10860
caagtgtttt ggctctcagg ccgaggccca cggcaagtat ttgggcaagg ggtcgctggt    10920
attcgtgcag ggcaagattc ggaataccaa gtacgagaag gacggccaga cggtctacgg    10980
gaccgacttc attgccgata aggtggatta tctggacacc aaggcaccag gcgggtcaaa    11040
tcaggaataa gggcacattg ccccggcgtg agtcggggca atcccgcaag gagggtgaat    11100
gaatcggacg tttgaccgga aggcatacag gcaagaactg atcgacgcgg ggttttccgc    11160
cgaggatgcc gaaaccatcg caagccgcac cgtcatgcgt gcgccccgcg aaaccttcca    11220
gtccgtcggc tcgatggtcc agcaagctac ggccaagatc gagcgcgaca gcgtgcaact    11280
ggctccccct gccctgcccg cgccatcggc cgccgtggag cgttcgcgtc gtctcgaaca    11340
ggaggcggca ggtttggcga agtcgatgac catcgacacg cgaggaacta tgacgaccaa    11400
gaagcgaaaa accgccggcg aggacctggc aaaacaggtc agcgaggcca agcaggccgc    11460
gttgctgaaa cacacgaagc agcagatcaa ggaaatgcag ctttccttgt tcgatattgc    11520
gccgtggccg gacacgatgc gagcgatgcc aaacgacacg gcccgctctg ccctgttcac    11580
cacgcgcaac aagaaaatcc cgcgcgaggc gctgcaaaac aaggtcattt tccacgtcaa    11640
caaggacgtg aagatcacct acaccggcgt cgagctgcgg gccgacgatg acgaactggt    11700
gtggcagcag gtgttggagt acgcgaagcg caccctatc ggcgagccga tcaccttcac     11760
gttctacgag ctttgccagg acctgggctg gtcgatcaat ggccggtatt acacgaaggc    11820
cgaggaatgc ctgtcgcgcc tacaggcgac ggcgatgggc ttcacgtccg accgcgttgg    11880
gcacctggaa tcggtgtcgc tgctgcaccg cttccgcgtc ctggaccgtg caagaaaac    11940
gtcccgttgc caggtcctga tcgacgagga aatcgtcgtg ctgtttgctg gcgaccacta    12000
cacgaaattc atatgggaga agtaccgcaa gctgtcgccg acggcccgac ggatgttcga    12060
ctatttcagc tcgcaccggg agccgtaccc gctcaagctg gaaaccttcc gcctcatgtg    12120
cggatcggat tccaccccgcg tgaagaagtg cgcgcagcag gtcggcgaag cctgcgaaga    12180
gttgcgaggc agcggcctgg tggaacacgc ctgggtcaat gatgacctgg tgcattgcaa    12240
acgctagggc cttgtggggt cagttccggc tgggggttca gcagccagcg ctttactggc    12300
atttcaggaa caagcgggca ctgctcgacg cacttgcttc gctcagtatc gctcgggacg    12360
cacggcgcgc tctacgaact gccgataaac agaggattaa aattgacaat tcaatggcaa    12420
ggactgccag cgctgccatt tttgggggtga ggccgttcgc ggccgagggg cgcagcccct    12480
gggggggatgg gaggcccgcg ttagcgggcc gggagggttc gagaagggg ggcaccccc     12540
ttcggcgtgc gcggtcacgc gcacagggcg cagccctggt taaaaacaag gtttataaat    12600
attggtttaa aagcaggtta aaagacaggt tagcggtggc cgaaaacggg cggaaaccc     12660
ttgcaaatgc tggattttct gcctgtggac agcccctcaa atgtcaatag gtgcgcccct    12720
```

| | | | | |
|---|---|---|---|---|
| catctgtcag | cactctgccc | ctcaagtgtc | aaggatcgcg | ccccctcatct gtcagtagtc 12780 |
| gcgcccctca | agtgtcaata | ccgcagggca | cttatcccca | ggcttgtcca catcatctgt 12840 |
| gggaaactcg | cgtaaaatca | ggcgttttcg | ccgatttgcg | aggctggcca gctccacgtc 12900 |
| gccggccgaa | atcgagcctg | ccctcatct | gtcaacgccg | cgccgggtga gtcggcccct 12960 |
| caagtgtcaa | cgtccgcccc | tcatctgtca | gtgagggcca | agttttccgc gaggtatcca 13020 |
| caacgccggc | ggccgcggtg | tctcgcacac | ggcttgacg | gcgtttctgg cgcgtttgca 13080 |
| gggccataga | cggccgccag | cccagcggcg | agggcaacca | gcccggtgag cgtcgcaaag 13140 |
| gcgctcggtc | ttgccttgct | cgtcgagatc | tggggtcgat | cagccgggga tgcatcaggc 13200 |
| cgacagtcgg | aacttcgggt | ccccgacctg | taccattcgg | tgagcaatgg ataggggagt 13260 |
| tgatatcgtc | aacgttcact | tctaaagaaa | tagcgccact | cagcttcctc agcggcttta 13320 |
| tccagcgatt | tcctattatg | tcggcatagt | tctcaagatc | gacagcctgt cacggttaag 13380 |
| cgagaaatga | ataagaaggc | tgataattcg | gatctctgcg | agggagatga tatttgatca 13440 |
| caggcagcaa | cgctctgtca | tcgttacaat | caacatgcta | ccctccgcga gatcatccgt 13500 |
| gtttcaaacc | cggcagctta | gttgccgttc | ttccgaatag | catcggtaac atgagcaaag 13560 |
| tctgccgcct | tacaacggct | ctcccgctga | cgccgtcccg | gactgatggg ctgcctgtat 13620 |
| cgagtggtga | ttttgtgccg | agctgccggt | cggggagctg | ttggctggct ggtggcagga 13680 |
| tatattgtgg | tgtaaacaaa | ttgacgctta | gacaacttaa | taacacattg cggacgtttt 13740 |
| taatgtactg | gggtggtttt | tcttttcacc | agtgagacgg | gcaacagctg attgcccttc 13800 |
| accgcctggc | cctgagagag | ttgcagcaag | cggtccacgc | tggtttgccc cagcaggcga 13860 |
| aaatcctgtt | tgatggtggt | tccgaaatcg | gcaaaatccc | ttataaatca aagaatagc 13920 |
| ccgagatagg | gttgagtgtt | gttccagttt | ggaacaagag | tccactatta aagaacgtgg 13980 |
| actccaacgt | caaagggcga | aaaccgtct | atcagggcga | tggcccacta cgtgaaccat 14040 |
| cacccaaatc | aagttttttg | gggtcgaggt | gccgtaaagc | actaaatcgg aaccctaaag 14100 |
| ggagcccccg | atttagagct | tgacggggaa | agccggcgaa | cgtggcgaga aggaaggga 14160 |
| agaaagcgaa | aggagcgggc | gccattcagg | ctgcgcaact | gttgggaagg g 14211 |

<210> SEQ ID NO 18
<211> LENGTH: 13102
<212> TYPE: DNA
<213> ORGANISM: Artificial Sequence
<220> FEATURE:
<223> OTHER INFORMATION: pBYKEHM-Bsa

<400> SEQUENCE: 18

| | | | | |
|---|---|---|---|---|
| cgatcggtcg | attcatagaa | gattagattt | ttcatagtat | ttttttaaag taaaccttta 60 |
| actacggtta | ggacactttt | aagttaaatt | taatttgaac | ccttaaatta attttttaaaa 120 |
| tagataaata | tcaatcatcc | tgatatgctt | ttgaaaaat | gaatgagaaa gatgattcaa 180 |
| ttaaggccac | attttaatca | tgactaaaat | aatatacagt | ataatttcat atatatttgc 240 |
| tttaaaaaaa | aattgacaat | ccattcgttt | ctagcaataa | atttcttcaa ccacaaatat 300 |
| attaaagata | actacggcat | agaaacaaaa | atctatgaag | aattttgta tacttcatat 360 |
| gaaattaaaa | aaaacttcat | tgaacatcaa | aataataata | ataatcataa actcctcaat 420 |
| atttatattc | ctagcttctt | gaattaaatt | gtttacatat | tcaacgatgt aaaaaattat 480 |
| ttctctatct | attttccttta | tatcatgcat | ggtttcacat | atatcaaagg ataaaagcaa 540 |

```
tctatgtaaa ttatctcact ttattaagtt ttctatctga attattgaga acgtagattt    600 cttttttgcac tatcccccaa taattagcaa aacacaccta gactagattt gttttgctaa    660
cccaattgat attaattata tatgattaat atttatatgt atatggaatt ggttaataaa    720
atgcatctgg ttcatcaaag aattataaag acacgtgaca ttcatttagg ataagaaata    780
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc ttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga accgaatac   1140 tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatcccta    1620 cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaaa gtctcaattg ccctttggtc ttctgagact gtatctttga   1920 tattttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt tttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaattaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgataa agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga acttttcaa caaagggtaa tatccgaaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
```

```
tcaaagatac agtctcagaa gaccaaaggg caattgagac ttttcaacaa agggtaatat    3000
ccggaaacct cctcggattc cattgcccag ctatctgtca ctttattgtg aagatagtgg    3060
aaaaggaagg tggctcctac aaatgccatc attgcgataa aggaaaggcc atcgttgaag    3120
atgcctctgc cgacagtggt cccaaagatg acccccacc cacgaggagc atcgtggaaa    3180
aagaagacgt tccaaccacg tcttcaaagc aagtggattg atgtgatatc tccactgacg    3240
taagggatga cgcacaatcc cactatcctt cgcaagaccc ttcctctata taaggaagtt    3300
catttcattt ggagaggacc tcgagaaaca acaaaatca acaaatatag aaaataacgc     3360
atttccaatt ctttgaaatt tctgcaacat ctagcgagac caacaacggt ctctagctaa    3420
agcagaatgc tgagctaaaa gaaaggcttt ttccattttc gagagacaat gagaaaagaa    3480
gaagaagaag aagaagaaga agaagaagaa aagagtaaat aataaagccc cacaggaggc    3540
gaagttcttg tagctccatg ttatctaagt tattgatatt gtttgcccta tattttattt    3600
ctgtcattgt gtatgttttg ttcagtttcg atctccttgc aaaatgcaga gattatgaga    3660
tgaataaact aagttatatt attatacgtg ttaatattct cctcctctct ctagctagcc    3720
ttttgttttc tcttttttctt atttgatttt ctttaaatca atccatttta ggagagggcc    3780
agggagtgat ccagcaaaac atgaagatta gaagaaactt ccctcttttt tttcctgaaa    3840
acaatttaac gtcgagattt atctcttttt gtaatggaat catttctaca gttatgacgg    3900
ctcactgagg aaatatatag acaaattaag tttggttcta tgagttctaa tttggactta    3960
agagttgttt gaaattctat tttatagtga tgcttataat gtatttggac tgttttctgc    4020
tgtgtgtaag acctttggt ctgtgaactg gaaacataca tgaataaatt tctttgaatt    4080
tactggaatt tttgcatcaa caaaagaaaa attgaagtta ctaacttgta aatggaacaa    4140
ttgtaatgtt aaaggatata aatatcttaa tatagtgcga tacgaatcac acgaatgcaa    4200
gactttctct ctctgctccc gctcatgctc tcggtgcatg ttagctaaat atacatcgtg    4260
gcatccatgg caggagcatg aggacgggga tgaggaaggg agtgaggagg gccaaaagaa    4320
gtacacatag tttcctttgg gagcgaattc tcgattaaaa atcccaatta tatttggtct    4380
aatttagttt ggtattgagt aaaacaaatt cgaaccaaac caaatataa atatatagtt     4440
tttatatata tgcctttaag acttttata gaattttctt taaaaaatat ctagaaatat    4500
ttgcgactct tctggcatgt aatatttcgt taaatatgaa gtgctccatt tttattaact    4560
ttaaataatt ggttgtacga tcactttctt atcaagtgtt actaaaatgc gtcaatctct    4620
ttgttcttcc atattcatat gtcaaaatct atcaaaattc ttatatatct ttttcgaatt    4680
tgaagtgaaa tttcgataat ttaaaattaa atagaacata tcattattta ggtatcatat    4740
tgattttttat acttaattac taaatttggt taactttgaa agtgtacatc aacgaaaaat    4800
tagtcaaacg actaaaataa ataaatatca tgtgttatta agaaaattct cctataagaa    4860
tattttaata gatcatatgt ttgtaaaaaa aattaatttt tactaacaca tatatttact    4920
tatcaaaaat ttgacaaagt aagattaaaa taatattcat ctaacaaaaa aaaaaccaga    4980
aaatgctgaa aacccggcaa aaccgaacca atccaaaccg atatagttgg tttggtttga    5040
ttttgatata aaccgaacca actcggtcca tttgcacccc taatcataat agctttaata    5100
tttcaagata ttattaagtt aacgttgtca atatcctgga aattttgcaa aatgaatcaa    5160
gcctatatgg ctgtaaatatg aatttaaaag cagctcgatg tggtggtaat atgtaattta    5220
cttgattcta aaaaaatatc ccaagtatta ataatttctg ctaggaagaa ggttagctac    5280
```

```
gatttacagc aaagccagaa tacaaagaac cataaagtga ttgaagctcg aaatatacga    5340
aggaacaaat atttttaaaa aaatacgcaa tgacttggaa caaaagaaag tgatatattt    5400
tttgttctta aacaagcatc ccctctaaag aatggcagtt ttcctttgca tgtaactatt    5460
atgctcccct cgttacaaaa attttggact actattggga acttcttctg aaaatagtgg    5520
taccgagtgt acttcaagtc agttggaaat caataaaatg attattttat gaatatattt    5580
cattgtgcaa gtagatagaa attacatatg ttacataaca cacgaaataa acaaaaaaac    5640
acaatccaaa acaaacaccc caaacaaaat aacactatat atatcctcgt atgaggagag    5700
gcacgttcag tgactcgacg attcccgagc aaaaaaagtc tccccgtcac acatatagtg    5760
ggtgacgcaa ttatcttcaa agtaatcctt ctgttgactt gtcattgata acatccagtc    5820
ttcgtcagga ttgcaaagaa ttatagaagg gattccacct tttattttct tcttttttcc    5880
atatttaggg ttgacagtga aatcagactg gcaacctatt aattgcttcc acaatgggac    5940
gaacttgaag gggatgtcgt cgatgatatt ataggtggcg tgttcatcgt agttggtgaa    6000
gtcgatggtc ccgttccagt agttgtgtcg cccgagactt ctagcccagg tggtctttcc    6060
ggtacgagtt ggtccgcaga tgtagaggct ggggtgtctg accccagtcc ttccctcatc    6120
ctggttagat cggccatcca ctcaaggtca gattgtgctt gatcgtagga gacaggatgt    6180
atgaaagtgt aggcatcgat gcttacatga tataggtgcg tctctctcca gttgtgcaga    6240
tcttcgtggc agcggagatc tgattctgtg aagggcgaca cgtactgctc aggttgtgga    6300
ggaaataatt tgttggctga atattccagc cattgaagct tgttgccca ttcatgaggg    6360 aactcttctt tgatcatgtc aagatactcc tccttagacg ttgcagtctg gataatagtt    6420
cgccatcgtg cgtcagattt gcgaggagac accttatgat ctcggaaatc tcctctggtt    6480
ttaatatctc cgtcctttga tatgtaatca aggacttgtt tagagtttct agctggctgg    6540
atattagggt gatttccttc aaaatcgaaa aagaaggat ctctaataca aggtttttta    6600
tcaagctgga taagagcatg atagtgggta gtgccatctt gatgaagctc agaagcaaca    6660
ccaaggaaga aaataagaaa aggtgtgagt ttctcccaga gaaactggaa taaatcatct    6720
ctttgagatg agcacttggg gtaggtaagg aaaacatatt tagattggag tctgaagttc    6780
ttgctagcag aaggcatgtt gttgtgactc cgaggggttg cctcaaactc tatcttataa    6840
ccggcgtgga ggcatggagg caagggcatt ttggtaattt aagtagttag tggaaaatga    6900
cgtcatttac ttaaagacga agtcttgcga caagggggc ccacgccaa ttttaatatt    6960 accggcgtgg ccccacctta tcgcgagtgc tttagcacga gcggtccaga tttaaagtag    7020
aaaagttccc gcccactagg gttaaaggtg ttcacactat aaaagcatat acgatgtgat    7080
ggtatttgat ggagcgtata ttgtatcagg tatttccgtc ggatacgaat tattcgtacg    7140
gccggaccgg tcccctaggc cggccaattc gagatcggcc gcggctgagt ggctccttca    7200
atcgttgcgg ttctgtcagt tccaaacgta aacggcttg tcccgcgtca tcggcggggg    7260
tcataacgtg actcccttaa ttctccgctc atgatcagat tgtcgtttcc cgccttcagt    7320
ttaaactatc agtgtttgac aggatatatt ggcgggtaaa cctaagagaa aagagcgttt    7380
attagaataa tcggatattt aaagggcgt gaaaaggttt atccgttcgt ccatttgtat    7440
gtgcatgcca accacagggt tccccagatc tggcgccggc cagcgagacg agcaagattg    7500
gccgccgccc gaaacgatcc gacagcgcgc ccagcacagg tgcgcaggca aattgcacca    7560
acgcatacag cgccagcaga atgccatagt gggcggtgac gtcgttcgag tgaaccagat    7620
cgcgcaggag gcccggcagc accggcataa tcaggccgat gccgacagcg tcgagcgcga    7680
```

```
cagtgctcag aattacgatc aggggtatgt tgggtttcac gtctggcctc cggagactgt    7740
catacgcgta aaaaggccgc gttgctggcg ttttttccata ggctccgccc ccctgacgag    7800
catcacaaaa atcgacgctc aagtcagagg tggcgaaacc cgacaggact ataaagatac    7860
caggcgtttc ccctggaag ctccctcgtg cgctctcctg ttccgaccct gccgcttacc    7920
ggatacctgt ccgcctttct cccttcggga agcgtggcgc tttctcatag ctcacgctgt    7980
aggtatctca gttcggtgta ggtcgttcgc tccaagctgg gctgtgtgca cgaaccccc    8040 gttcagcccg accgctgcgc cttatccggt aactatcgtc ttgagtccaa cccggtaaga    8100
cacgacttat cgccactggc agcagccact ggtaacagga ttagcagagc gaggtatgta    8160
ggcggtgcta cagagttctt gaagtggtgg cctaactacg gctacactag aaggacagta    8220
tttggtatct gcgctctgct gaagccagtt accttcggaa aaagagttgg tagctcttga    8280
tccggcaaac aaaccaccgc tggtagcggt ggttttttg tttgcaagca gcagattacg    8340
cgcagaaaaa aaggatctca agaagatcct ttgatctttt ctacggggtc tgacgctcag    8400
tggaacgaaa actcacgtta agggattttg gtcatgagat tatcaaaaag gatcttcacc    8460
tagatccttt taaattaaaa atgaagtttt aaatcaatct aaagtatata tgagtaaact    8520
tggtctgcag ttgccatgtt ttacggcagt gagagcagag atagcgctga tgtccggcgg    8580
tgcttttgcc gttacgcacc accccgtcag tagctgaaca ggaggacag ctgatagaca    8640 cagaagccac tggagcacct caaaaacacc atcatacact aaatcagtaa gttggcagca    8700
tcacccataa ttgtggtttc aaaatcggct ccgtcgatac tatgttatac gccaactttg    8760
aaaacaactt tgaaaaagct gttttctggt atttaaggtt ttagaatgca aggaacagtg    8820
aattggagtt cgtcttgtta taattagctt cttggggtat cttaaaatac tgtagaaaag    8880
aggaaggaaa taataaatgg ctaaaatgag aatatcaccg gaattgaaaa aactgatcga    8940
aaaataccgc tgcgtaaaag atacggaagg aatgtctcct gctaaggtat ataagctggt    9000
gggagaaaat gaaaacctat atttaaaaat gacggacagc cggtataaag ggaccaccta    9060
tgatgtggaa cgggaaaagg acatgatgct atggctggaa ggaaagctgc ctgttccaaa    9120
ggtcctgcac tttgaacggc atgatggctg gagcaatctg ctcatgagtg aggccgatgg    9180
cgtcctttgc tcggaagagt atgaagatga acaaagccct gaaaagatta tcgagctgta    9240
tgcggagtgc atcaggctct ttcactccat cgacatatcg gattgtccct atacgaatag    9300
cttagacagc cgcttagccg aattggatta cttactgaat aacgatctgg ccgatgtgga    9360
ttgcgaaaac tgggaagaag acactccatt taaagatccg cgcgagctgt atgatttttt    9420
aaagacggaa aagcccgaag aggaacttgt cttttcccac ggcgacctgg agacagcaa    9480 catctttgtg aaagatggca aagtaagtgg ctttattgat cttgggagaa gcggcagggc    9540
ggacaagtgg tatgacattg ccttctgcgt ccggtcgatc agggaggata tcggggaaga    9600
acagtatgtc gagctatttt ttgacttact ggggatcaag cctgattggg agaaaataaa    9660
atattatatt ttactggatg aattgttta gtacctagat gtggcgcaac gatgccggcg    9720
acaagcagga gcgcaccgac ttcttccgca tcaagtgttt tggctctcag gccgaggccc    9780
acggcaagta tttgggcaag gggtcgctgg tattcgtgca gggcaagatt cggaatacca    9840
agtacgagaa ggacggccag acggtctacg ggaccgactt cattgccgat aaggtggatt    9900
atctggacac caaggcacca ggcgggtcaa atcaggaata agggcacatt gccccggcgt    9960
gagtcggggc aatcccgcaa ggagggtgaa tgaatcggac gtttgaccgg aaggcataca    10020
```

```
ggcaagaact gatcgacgcg gggttttccg ccgaggatgc cgaaaccatc gcaagccgca    10080
ccgtcatgcg tgcgccccgc gaaaccttcc agtccgtcgg ctcgatggtc cagcaagcta    10140
cggccaagat cgagcgcgac agcgtgcaac tggctccccc tgccctgccc gcgccatcgg    10200
ccgccgtgga gcgttcgcgt cgtctcgaac aggaggcggc aggtttggcg aagtcgatga    10260
ccatcgacac gcgaggaact atgacgacca agaagcgaaa aaccgccggc gaggacctgg    10320
caaaacaggt cagcgaggcc aagcaggccg cgttgctgaa acacacgaag cagcagatca    10380
aggaaatgca gctttccttg ttcgatattg cgccgtggcc ggacacgatg cgagcgatgc    10440
caaacgacac ggcccgctct gccctgttca ccacgcgcaa caagaaaatc ccgcgcgagg    10500
cgctgcaaaa caaggtcatt ttccacgtca acaaggacgt gaagatcacc tacaccggcg    10560
tcgagctgcg ggccgacgat gacgaactgg tgtggcagca ggtgttggag tacgcgaagc    10620 gcaccccta t cggcgagccg atcaccttca cgttctacga gctttgccag gacctgggct    10680
ggtcgatcaa tggccggtat tacacgaagg ccgaggaatg cctgtcgcgc ctacaggcga    10740
cggcgatggg cttcacgtcc gaccgcgttg ggcacctgga atcggtgtcg ctgctgcacc    10800
gcttccgcgt cctggaccgt ggcaagaaaa cgtcccgttg ccaggtcctg atcgacgagg    10860
aaatcgtcgt gctgtttgct ggcgaccact acacgaaatt catatgggag aagtaccgca    10920
agctgtcgcc gacggcccga cggatgttcg actatttcag ctcgcaccgg agccgtacc    10980 cgctcaagct ggaaaccttc cgcctcatgt gcggatcgga ttccacccgc gtgaagaagt    11040
ggcgcgagca ggtcggcgaa gcctgcgaag agttgcgagg cagcggcctg gtggaacacg    11100
cctgggtcaa tgatgacctg gtgcattgca acgctaggg ccttgtgggg tcagttccgg    11160
ctgggggttc agcagccagc gctttactgg catttcagga acaagcgggc actgctcgac    11220
gcacttgctt cgctcagtat cgctcggac gcacggcgcg ctctacgaac tgccgataaa    11280
cagaggatta aaattgacaa ttcaatggca aggactgcca gcgctgccat ttttggggtg    11340
aggccgttcg cggccgaggg gcgcagcccc tgggggatg ggaggccgc gttagcgggc     11400 cgggagggtt cgagaagggg gggcaccccc cttcggcgtg cgcggtcacg cgcacagggc    11460
gcagccctgg ttaaaaacaa ggtttataaa tattggttta aaagcaggtt aaaagacagg    11520
ttagcggtgg ccgaaaaacg ggcggaaacc cttgcaaatg ctggattttc tgcctgtgga    11580
cagcccctca aatgtcaata ggtgcgcccc tcatctgtca gcactctgcc cctcaagtgt    11640
caaggatcgc gcccctcatc tgtcagtagt cgcgcccctc aagtgtcaat accgcagggc    11700
acttatcccc aggcttgtcc acatcatctg tgggaaactc gcgtaaaatc aggcgttttc    11760
gccgatttgc gaggctggcc agctccacgt cgccggccga aatcgagcct gcccctcatc    11820
tgtcaacgcc gcgccgggtg agtcggcccc tcaagtgtca acgtccgccc tcatctgtc    11880 agtgagggcc aagttttccg cgaggtatcc acaacgccgg cggccgcggt gtctcgcaca    11940
cggcttcgac ggcgtttctg gcgcgtttgc agggccatag acggccgcca gcccagcggc    12000
gagggcaacc agcccggtga gcgtcgcaaa ggcgctcggt cttgccttgc tcgtcgagat    12060
ctggggtcga tcagccgggg atgcatcagg ccgacagtcg gaacttcggg tccccgacct    12120
gtaccattcg gtgagcaatg gataggggag ttgatatcgt caacgttcac ttctaaagaa    12180
atagcgccac tcagcttcct cagcggcttt atccagcgat ttcctattat gtcggcatag    12240
ttctcaagat cgacagcctg tcacggttaa gcgagaaatg aataagaagg ctgataattc    12300
ggatctctgc gagggagatg atatttgatc acaggcagca acgctctgtc atcgttacaa    12360
tcaacatgct accctccgcg agatcatccg tgtttcaaac ccggcagctt agttgccgtt    12420
```

```
cttccgaata gcatcggtaa catgagcaaa gtctgccgcc ttacaacggc tctcccgctg    12480
acgccgtccc ggactgatgg gctgcctgta tcgagtggtg attttgtgcc gagctgccgg    12540
tcggggagct gttggctggc tggtggcagg atatattgtg gtgtaaacaa attgacgctt    12600
agacaactta ataacacatt gcggacgttt ttaatgtact ggggtggttt ttcttttcac    12660
cagtgagacg ggcaacagct gattgccctt caccgcctgg ccctgagaga gttgcagcaa    12720
gcggtccacg ctggtttgcc ccagcaggcg aaaatcctgt ttgatggtgg ttccgaaatc    12780
ggcaaaatcc cttataaatc aaaagaatag cccgagatag ggttgagtgt tgttccagtt    12840
tggaacaaga gtccactatt aaagaacgtg gactccaacg tcaaagggcg aaaaaccgtc    12900
tatcagggcg atgcccact  acgtgaacca tcacccaaat caagtttttt ggggtcgagg    12960
tgccgtaaag cactaaatcg gaaccctaaa gggagccccc gatttagagc ttgacgggga    13020
aagccggcga acgtggcgag aaaggaaggg aagaaagcga aaggagcggg cgccattcag    13080
gctgcgcaac tgttgggaag gg                                            13102
```

OPTIMIZED PLANT EXPRESSION SYSTEMS

RELATED APPLICATIONS

This application claims the benefit of U.S. provisional patent application 62/984,491, filed Mar. 3, 2020 titled "Optimized Plant Expression Systems for High Level Production of Monoclonal Antibodies and Methods of Production Thereof," the entirety of the disclosure of which is hereby incorporated by this reference.

This application is also a continuation-in-part application of pending U.S. patent application Ser. No. 17/073,102, filed Oct. 16, 2020, which claims the benefit of U.S. provisional patent application 62/916,211, filed Oct. 16, 2019, and a continuation-in-part application of pending U.S. patent application Ser. No. 16/976,739, filed Aug. 28, 2020, which is the U.S. National Stage of International Application No. PCT/US2019/020621, filed Mar. 4, 2019, which claims the benefit of U.S. Provisional Patent Application No. 62/638,010, filed Mar. 2, 2018, wherein the entireties of all disclosures are hereby incorporated by this reference thereto.

STATEMENT REGARDING FEDERALLY FUNDED RESEARCH OR DEVELOPMENT

This invention was made with government support under R33 AI101329 awarded by the National Institutes of Health. The government has certain rights in the invention.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 61,213 byte ASCII (text) file named "SeqList" created on Feb. 23, 2021.

TECHNICAL FIELD

The disclosure relates to plant expression vectors produce heteromultimeric proteins and that allow co-expression of multiple genes in a single expression vector.

BACKGROUND

Plant-based biopharmaceuticals can be made in plant cells, tissues, or whole plants that are either stably transformed with the target gene or expressed transiently via agroinfiltration. Since the viability of plant-based expression systems depends strongly on the yield of the target product, efforts to increase the expression of a desired protein have focused on rigorously optimizing every step in the lifecycle of the target gene product, from delivery of the transgene to the plant cell to the purification of the fully assembled protein.

Antibody-based therapeutics are the largest sector of the global biopharmaceutical market, with sales exceeding 100 billion USD worldwide and sales predicted to reach 137-200 billion USD by 2022. While most biopharmaceuticals have traditionally been produced in mammalian cell culture systems, plant-based recombinant expression systems have demonstrated significant advantages. Like mammalian systems, plants can carry out complex post-translational modifications necessary for the function of many biopharmaceuticals. However, unlike mammalian systems, which require large investment and operating costs, plant systems do not require expensive cell-culture facilities and bioreactors. Furthermore, plant systems do not need to be grown in sterile conditions and, as plants lack animal pathogens, plant-based biotechnology has improved intrinsic safety over mammalian expression systems. These factors allow highly scalable production of biopharmaceutical proteins with substantially reduced costs. The cost-effectiveness of plant-based systems may especially benefit developing countries.

In addition, advances in plant engineering have resulted in the ability to produce tailor-made glycans. The glycosylation state of the antibody is crucial for its stability and function. In comparison to mammalian cells which have highly heterogeneous glycoforms that may be detrimental for biopharmaceutical production, advances in plant glycoengineering have allowed the production of monoclonal antibodies (mAbs) with more homogenous human-like glycans. By removing the endogenous plant-specific β1,2-linked xylose and α1,3-linked fucose, a variety of plant-made antibodies have demonstrated improved immune receptor binding and greater potency compared to commercially available antibodies produced in mammalian cells. Remarkably, the entire human sialyation pathway has been transferred into plants. These advances in glycoengineering have been used in several practical applications. Antibodies made in glycoengineered plants have been successfully used to treat Ebola virus disease in rhesus macaques and humans and the first in-human clinical trials have been carried out using plant-made antibodies. High expressing, safe, and efficacious plant-made antibody therapies have also been developed for dengue virus, West Nile virus, and chikungunya virus, while a variety of antibody-based immune complex vaccines have been developed in plants and shown promising efficacy in mouse immunization trials.

Unfortunately, plant production of heteromultimeric proteins of pharmaceutical use are often toxic to plant. Accordingly, plant expression of such proteins, such as antibody for therapeutic use, need further optimization for improved production.

SUMMARY

Mammalian cells are traditionally used for monoclonal antibody production; however, plant-based expression systems have significant advantages. Described herein are plant transient expression systems using optimized geminiviral vectors that can efficiently produce heteromultimeric proteins. Specifically, described herein are optimized plant expression BeYDV vectors that can simultaneously coexpress high levels (yields of 3-5 g/kg leaf fresh weight or ~50% total soluble protein) of two, three, or four fluorescent proteins in a noncompetitive manner. In some aspects, the optimized plant expression BeYDV vector has near equal expression of each protein encoded in the vector. This technology is a versatile tool for the production of a wide spectrum of pharmaceutical multi-protein complexes in a fast, powerful, and cost-effective way.

In one aspects, the geminiviral vector described herein comprises a first long intergenic region of bean yellow dwarf virus (LIR); a first nucleotide sequence encoding at least one transgene; a short intergenic region of bean yellow dwarf virus (SIR); a second LIR; and a second nucleotide sequence encoding the Rep/RepA of BeYDV, wherein the second nucleotide sequence is between the SIR and second LIR. The first nucleotide sequence further comprises at least one optimized 5' untranslated region (5' UTR) and at least one optimized 3' untranslated region (3'UTR). The optimized 5' UTR comprises a 35S promoter with duplicated enhancer region from cauliflower mosaic virus and at least one 5' UTR selected from the group consisting of: the psaK gene of *Nicotinana benthamiana*, tobacco mosaic virus, tobacco etch virus, and alfalfa mosaic virus. The optimized 3' UTR comprises at least one terminator sequence selected from the group consisting of: tobacco extension terminator with its intron removed, the 3'UTR from ACT3 gene of *N. benthamiana*, tobacco Rb7 matrix attachment region, 3' UTR from pea rbcS gene, and the 3' UTR from soybean vspB gene. In some aspects vector produces a heteromultimeric protein and thus comprises a plurality of transgenes encoding the subunits of the heteromultimeric protein. Each transgene comprises the optimized 5'UTR and the optimized 3'UTR. In certain embodiments, the optimized 5'UTR and the optimized 3'UTR of the plurality of transgenes are different. For example, where the vector produces an antibody, the first nucleotide sequence comprises a sequence encoding the light chain of the antibody and a sequence encoding the heavy chain of the antibody, wherein the sequence encoding the light chain of the antibody comprises the optimized 5' UTR and the optimized 3'UTR and the sequence encoding the heavy chain of the antibody comprises the optimized 5' UTR and the optimized 3'UTR. In a particular embodiment, the optimized 5'UTR and the optimized 3'UTR of the sequence encoding the light chain of the antibody and the sequence encoding the heavy chain of the antibody are different.

In other aspects, the geminiviral vector further comprises a third LIR, a second SIR; and a third nucleotide sequence encoding at least one transgene. The first nucleotide sequence further comprises an optimized 5' untranslated region (5' UTR) and an optimized 3' untranslated region (3'UTR). The optimized 5' UTR comprises a 35S promoter with duplicated enhancer region from cauliflower mosaic virus and at least one 5' UTR selected from the group consisting of: the psaK gene of *Nicotinana benthamiana*, tobacco mosaic virus, tobacco etch virus, and alfalfa mosaic virus. The optimized 3' UTR comprises at least one terminator sequence selected from the group consisting of: tobacco extension terminator with its intron removed, the 3'UTR from ACT3 gene of *N. benthamiana*, tobacco Rb7 matrix attachment region, 3' UTR from pea rbcS gene, and the 3' UTR from soybean vspB gene. In such embodiments, the second SIR is downstream of the first nucleotide sequence and upstream of the third LIR. The third nucleotide sequence is downstream of the third LIR and upstream of the first SIR, the second nucleotide sequence and the second LIR. In certain embodiments, the vector produces a heteromultimeric protein, and the first nucleotide sequence and the third nucleotide sequence encode at least one subunit of the heteromultimeric protein. The first nucleotide sequence and the third nucleotide sequence encode different subunits of the heteromultimeric protein. For example, where the vector produces an antibody, the first nucleotide sequence and the third nucleotide sequence encode the light chain and the heavy chain of the antibody. In particular embodiments, the first nucleotide sequence encodes the heavy chain of the antibody and the third nucleotide sequence encodes the light chain of the antibody.

In some implementations, the 5' UTR from the psaK gene of *N. benthamiana* is truncated. In some implementations, the tobacco Rb7 matrix attachment region is modified with unwanted restriction enzyme sites removed. In some implementations, the 3' UTR comprises the tobacco extension terminator with its intron removed, the 3'UTR from the ACT3 gene of *N. benthamiana*, and the tobacco Rb7 matrix attachment region. In some implementations, the 3' UTR comprises the tobacco extension terminator with its intron removed and the tobacco Rb7 matrix attachment region.

In some aspects, the optimized 5' UTR has at least 99% identity to nt 2192-3414 of SEQ ID NO. 16, nt 2192-3320 of SEQ ID NO. 17, or nt 2192-3320 of SEQ ID NO. 18. In some aspects, at least one portion of the sequence of the optimized 3' UTR has at least 99% identity to nt 4345-5317 of SEQ ID NO. 16, nt 7119-9536 of SEQ ID NO. 16, nt 4219-5735 of SEQ ID NO. 17, nt 5984-6632 of SEQ ID NO. 17, nt 3414-3714 of SEQ ID NO. 18, or nt 4345-5523 of SEQ ID NO. 18.

In certain embodiments, the vectors are designed from a vector backbone selected from the group consisting of: pBYKEHM-Bsa, pBYKEAM-BAGFPas6H, and pBY11HA-GFP. For example, the sequence of the vector comprises a portion with at least 95% or at least 99% sequence identity to nt 1-3424 of SEQ ID NOS. 16-18; and a portion with at least 95% or at least 99% sequence identity to nt 4247-14211 of SEQ ID NOS. 17 and 18 or nt 7107-17111 of SEQ ID NO. 16.

Various antibodies were produced using the optimized vectors with special focus given to the creation and production of a chimeric broadly neutralizing anti-flavivirus antibody. The variable regions of this murine antibody, 2A10G6, were codon optimized and fused to a human IgG1. Thus, also described herein are methods of producing a humanized antibody. In an exemplary embodiment, the method comprises introducing into an *agrobacterium* the geminiviral vector described herein, infiltrating a plant part with the *agrobacterium* containing the binary vector to produce a transformed plant part, extracting crude protein from the transformed plant part; and purifying the extracted crude protein.

Analysis of the chimeric antibody showed that it was efficiently expressed in plants at 1.5 grams of antibody/kilogram of leaf tissue, can be purified to near homogeneity by a simple one-step purification process, retains its ability to recognize the Zika virus envelope protein, and potently neutralizes Zika virus. Two other monoclonal antibodies were produced at similar levels (1.2-1.4 g/kg). Using these optimized vectors, milligram quantities of three different mAbs can be produced from a single plant leaf. Accordingly, also described herein are methods for producing in plants a chimeric antibody, for example, a chimeric antibody against a highly conserved fusion loop epitope found on flaviviruses. Notably, the plant-expressed antibodies producing according to the methods and expression systems described herein are correctly assembled, can be purified to near-homogeneity with a simple purification procedure, and retains the binding ability of the original murine antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts a generalized schematic of the plant expression vectors described herein. pBYKEAM is a replicating plant expression vector based on BeYDV with optimized 5' and 3' UTRs and is the vector of choice for high expression of a single target gene. pBYKEAM2 allows simultaneous coexpression of two genes from a single replicon containing optimized 5' and 3' UTRs. pBYKEMd2 is a previous iteration of pBYKEAM2 that does not contain double terminators. The remaining vectors contain multiple expression cassettes arranged as either a single large replicon or multiple replicons (when the gene cassettes are separated by SIR/LIR) with unoptimized 5' and 3' UTRs. For expression of antibodies, the barley alpha amylase signal sequence for ER-targeting is also present at the start of the gene. Abbreviations: LIR, the long intergenic region from BeYDV; 35S, the 35S promoter with duplicated enhancer region from cauliflower mosaic virus; PsaK2T 5', the truncated 5' UTR from the *Nicotiana benthamiana* psaK gene; Ext 3', the tobacco extensin terminator with intron removed; NbACT 3', the 3' UTR from the *N. benthamiana* ACT3 gene; Rb7 MAR, the tobacco Rb7 matrix attachment region; Rb7 MARd, a truncation of the Rb7 MAR to remove unwanted restriction enzyme sites; SIR, the short intergenic region from BeYDV; Rep/RepA, the replication proteins from BeYDV; TMV 5', the 5' UTR from tobacco mosaic virus; RbcS 3', the 3' UTR from the pea rbcS gene; VspB 3', the 3' UTR from the soybean vspB gene; AMV 5', the 5' UTR from alfalfa mosaic virus; TEV 5', the 5' UTR from tobacco etch virus; YFG, insertion site for the gene of interest; GFP, green fluorescent protein; DsR, DsRed fluorescent protein; YFP, yellow fluorescent protein; CFP, cyan fluorescent protein; 6D8H, the 6D8 heavy chain; 6D8L, the 6D8 light chain.

FIGS. 2A-2C demonstrate, in accordance with certain embodiments, simultaneous coexpression of up to four proteins with comparisons of optimized BeYDV vectors to unoptimized BeYDV vectors. Leaves of *N. benthamiana* were agroinfiltrated with either optimized (pBYKEAM or pBYKEAM2) vectors or unoptimized vectors (pBY-GR, pBY-GCR, referred to as "old") for GFP, DsRed, CFP, and YFP in various combinations. FIG. 2A depicts an exemplary leaves imaged at 5 days post infiltration (DPI) under a UV illumination. FIG. 2B depicts protein isolated from the plant leaves separated by nonreducing or reducing SDS-PAGE and either viewed under UV transillumination or stained with Coomassie gel. Rubisco large subunit (RbcL) and the monomeric-sized band of all fluorescent proteins are indicated. FIG. 2C depicts the relative total expression of each combination of constructs was analyzed using ImageJ software to quantify the band intensity of SDS-PAGE reducing gels. The mean band intensity is given ±standard error from 3 independently infiltrated leaf samples, where the expression of pBYKEAM-GFP was arbitrarily defined as 1. The bar colors are estimates of the relative production of each construct by non-reducing SDS-PAGE followed by ImageJ analysis using 3 independently infiltrated leaf samples. Statistical significance was calculated using student's t-test.

FIGS. 3A-3C depict, in accordance with certain embodiments, the role of replicon size and configuration in expression and replication of BeYDV vectors. Leaf DNA was extracted at 3 DPI from uninfiltrated (Wt), or samples infiltrated with the indicated vectors, then digested with indicated restriction enzymes (K, KpnI; S, SacI) and run on a 1% agarose gel (FIG. 3A). G(SL)R refers to pBY-G(SL)R; GR refers to pBY-G(SL)R. Replicon positions are indicated with arrow head. FIG. 3B depicts the fluorimetric analysis of GFP and DsRed accumulation showing efficient co-expression of two fluorescent proteins from either single [pBY-GR] or dual [pBY-G(SL)R]replicon vectors. Dilutions of total soluble protein extracts were subjected to spectrofluorometry using excitation and emission wavelengths of 485 nm and 538 nm for GFP, and 544 nm and 590 nm for DsRed. G(SL)R, pBY-G(SL)R; GR, pBY-G(SL)R. Data are means±S.D. from three independently infiltrated samples. FIG. 3C depicts separation of DNA isolated from leaves of uninfiltrated (Wt) or infiltrated with the indicated vectors on a 0.8% agarose gels before and after restriction enzyme digestion. GFP+CFP+DsRed indicates co-infiltrated sample with *Agrobacterium* mixture of pBY-GFP, pBY-CFP and pBY-DsRed. Note that construct pBY-DsRed does not contain Rep/RepA gene. Restriction enzyme XhoI was used for pBY-GFP, pBY-CFP, pBY-DsRed, pBY-GR, and GFP+CFP+DsRed. For pBY-GCR, restriction enzyme SalI was used. Expected replicon positions are indicated with arrow heads.

FIG. 4 depicts, in accordance with certain embodiments, simultaneous coexpression of three fluorescent proteins. *N. benthamiana* leaves were infiltrated with *Agrobacterium* strains harboring expression vectors as indicated (on the left). At 2 DPI the infiltrated leaf samples were examined with confocal laser scanning microscope. For co-infiltration, mixture of *Agrobacterium* strains harboring pBY-GFP, pBY-CFP, and pBY-DsRed were used. Excitation lasers of 488 nm, 458 nm, and 543 nm and detection windows of 550-560 nm, 470-500 nm, and 614-646 nm were employed to detect GFP, CFP, and DsRed signals, respectively. For plant autofluorescence chlorophyll detection, the excitation laser of 633 nm with detection window of 630-700 nm was used.

FIG. 5 depicts, in accordance with certain embodiments, the IgG production of three mAbs using optimized plant-expression vectors. Leaves of *N. benthamiana* agroinfiltrated with unoptimized (6D8 old) or optimized (6D8, HSV8, c2A10G6) BeYDV vectors were harvested at 5 DPI and protein extracts were analyzed for IgG production by ELISA using human IgG as a reference standard. Columns represent results from three independently infiltrated leaf samples standard error.

FIGS. 6A-6D depict, in accordance with certain embodiments, a western blot analysis of plant-derived 6D8. Protein samples were separated on a 4-20% SDS-PAGE gradient gel under denaturing and reducing condition (FIGS. 6A and 6B) or under non-reducing condition (FIG. 6C) and blotted onto a PVDF membrane. The membrane was incubated with a goat anti-human gamma chain antibody or goat anti-human kappa chain antibody to detect heavy chain (FIG. 6AA) or light chain (FIGS. 6B and 6C). Wt: Protein samples extracted from uninfiltrated leaves; lanes marked pBYR-H (SL)L: protein samples extracted from the leaves infiltrated with dual replicon construct pBYR-H(SL)L; lanes marked pBYR-HL: protein extracted from the single replicon construct pBYR-HL. FIG. 6D depicts the Commassie blue stained gel to show normalized total protein loading.

FIGS. 7A-7D depict, in accordance with certain embodiments, the characterization of c2A10G6. An exemplary *N. benthamina* leaf at 4 DPI was examined for signs of chlorosis or necrosis (FIG. 7A). On the exemplary leaf, faint chlorosis was visible, but there was no visible necrosis. To test whether the clarified leaf extracts of the antibody constructs were stable upon acid-precipitation, 1N phosphoric acid was added to a final acid volume of 4% of the total soluble extract. Following a six-minute incubation, the samples were neutralized with 1M Tris base. For comparison, a sample of the leaf extract pre-acid precipitation was also included along with a control uninfiltrated leaf extract that was not treated with acid. All three samples were mixed with non-reducing sample buffer and loaded on a 4-15% polyacrylamide gel for analysis by Coomassie-staining (FIG. 7B). The same samples of FIG. 7A were run on a 4-15% polyacrylamide gel for analysis by Western blot. The Western blot was detected with HRP-conjugated goat anti-human IgG (kappa only) (FIG. 7C). After protein G affinity purification, samples of the purified antibody were run on SDS-PAGE gels under non-reducing or reducing conditions as noted (FIG. 7D). The left panel shows the results following a silver stain. Only the c2A10G6 band is visible. The two panels on the right show the results of the purified antibody run under non-reducing and reducing conditions on a stain-free gel. Abbreviations: S, soluble fraction pre-acid precipitation; AP, samples subjected to acid-precipitation; U, uninfiltrated clarified leaf extract; NR, non-reducing conditions; R, reducing conditions.

FIGS. 8A and 8B depict, in accordance with certain embodiments, the binding of c2A10G6 to ZIKV envelope glycoprotein. Varying dilutions of clarified protein extract containing ZsE was directly bound to a polystyrene plate and probed with purified c2A10G6 to assess whether the antibody recognized the fusion loop epitope (FIG. 8A). Bound antibody was detected with goat anti-human IgG (kappa only) HRP conjugate. An uninfiltrated negative control was included to assess the level of any non-specific binding to native plant proteins. The ability of c2A10G6 to recognize the fusion loop epitope was analyzed via a western blot. Clarified protein extracts containing ZprME or an uninfiltrated control were probed with purified c2A10G6 and detected with HRP-conjugated goat anti-human IgG antibody (FIG. 8B).

FIG. 9 depicts the map of pBY11HA-GFP (sequence set forth in SEQ ID NO. 16), which contains a BeYDV replicon that lies between the 2 long intergenic regions (LIR), bounded by AscI and AgeI sites. The replicon contains 2 expression cassettes, both having the CaMV 35S dual-enhancer promoter (P 35Sx2e) followed by the N. benthamiana PsaK2 gene 5'UTR. The first cassette has 2 BsaI sites downstream of the 5'UTR; when cleaved by BsaI, the vector ends have 5' single strand protrusions (cohesive ends) 5'-CTAG (upstream) and 5'-AGCT (downstream), that permit insertion of a coding sequence. The BsaI sites are followed by a chimeric terminator comprising the tobacco extensin (Ext 3'UTR) and N. benthamiana HSP20 gene terminators, which is followed by the tobacco Rb7 matrix attachment region (MARc). Downstream of the first MARc lies the BeYDV short intergenic region (SIR), which also contains polyadenylation signals. The second expression cassette follows in tandem (P 35Sx2e, PsaK2 5'UTR), followed by the GFP coding sequence, which is flanked by unique XbaI and SacI sites. Just downstream lie a chimeric terminator comprising the tobacco extensin (here labelled "EU", but having the same sequence as the one in the first cassette) and N. benthamiana actin 3 (NbAct3) terminators. Another MARc and SIR segment follow the terminators. The Rep/RepA (C1/C2) gene in the inverse orientation is driven by a BeYDV promoter in the downstream LIR. An expression cassette for the siRNA binding protein p19 (from tomato bushy stunt virus) is located between the PvuI and AscI sites (~0-45° on the circular map). The p19 coding sequence is driven by a single enhancer 35S promoter and the tobacco mosaic virus (TMVΩ) 5'UTR. The potato pinII gene 3' region serves as the terminator for the p19 expression cassette. The T-DNA region (DNA that is transferred into plant cells by Agrobacterium tumefaciens) is delineated by the left border (LB) and right border segments.

DETAILED DESCRIPTION

Figure 1:
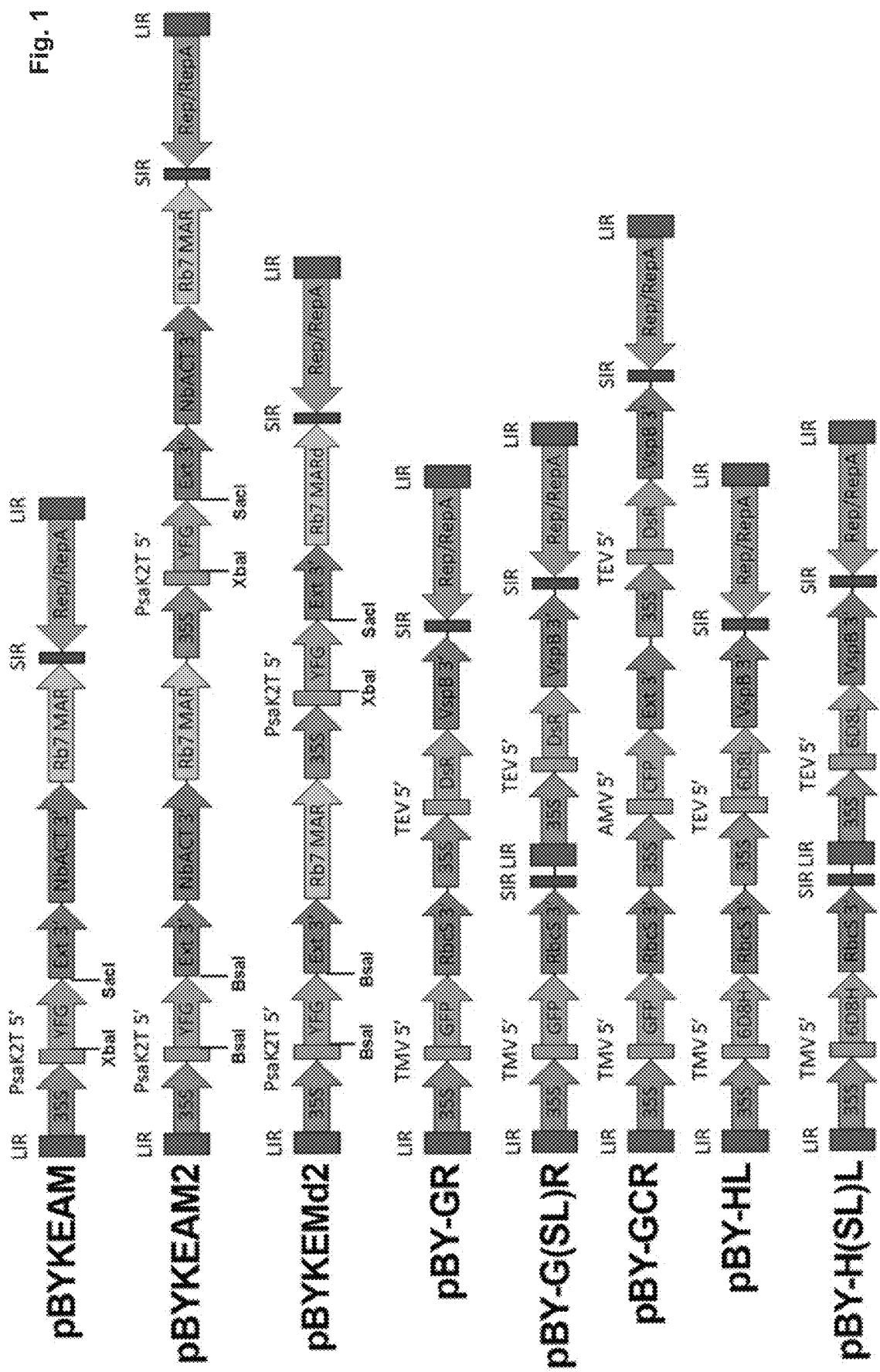

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, bean yellow dwarf virus may be abbreviated "BeYDV", monoclonal antibody as "mAb", Zika virus as "ZIKV", green fluorescent protein as "GFP", yellow fluorescent protein as "YFP", cyan fluorescent protein as "CFP", total soluble protein as "TSP", and leaf tissue fresh weight as "LFW".

As used herein, the term "terminator" or "terminator sequence" refers to a DNA sequence that causes the dissociation of RNA polymerase from DNA and hence terminates transcription of DNA into mRNA.

Plant expression systems have properties which make them uniquely suited to produce certain biopharmaceuticals. For example, when made in mammalian cells, the production of glucocerebrosidase as an enzyme replacement therapy for Gaucher's disease required costly in vitro glycosylation. However, as plants already contained the required glycoform, plant-based production of glucocerebrosidase reduced costs as well as potentially improved consistency and efficacy. These advances led to the first FDA approval of a plant-based therapeutic, while further research has led to the development of a lyophilized carrot cell juice which restores healthy enzyme levels in patients when consumed orally. As another example of the unique potential of plant systems, an anti-cancer lectin that was found to be toxic to mammalian cells and that was not properly folded in E. coli could instead be efficiently produced in plants, with an estimated 80% reduction in costs and 3-fold improved potency. Similarly, while human phosphatase and actin regulator 1 (PHACTR1) is difficult to express in mammalian cells due to a large number of interacting partners and cannot be properly folded in bacterial systems, it can be efficiently made in plants. The advances in the field of plant-made antibodies can be clearly seen by the first in-human clinical trial of the anti-cancer antibody 2G12 made in transgenic tobacco plants. Recently, a plant-made quadrivalent influenza VLP vaccine showed sustained, strong cross-reactive immune responses and has advanced to phase 3 clinical trials.

As shown in the aforementioned examples, co-expression of two or more proteins is required to produce biologically active pharmaceutical proteins, such as monoclonal antibodies, IgA, or multi-component virus like particles. Plant expression of heteromultimeric therapeutic proteins, however, remains a problem. Expression of these proteins in existing plant expression vectors are toxic to the plants.

Described herein is a plant expression system based on the geminivirus bean yellow dwarf virus (BeYDV) that replicates a target gene (for example a transgene encoding a protein or a portion of a protein) to a high copy number in the plant nucleus without causing toxicity. The vector based on BeYDV comprises at least two long intergenic regions of BeYDV (LIR) and at least one short intergenic region of BeYDV (SIR). For example, the replicon comprises the first LIR, a nucleotide sequence encoding at least one transgene, the SIR, a nucleotide sequence encoding the Rep/RepA of BeYDV, followed by the second LIR. In some embodiments, the vector based on BeYDV comprises three LIRs and two SIRs. For example, the replicon comprises the first LIR, a first nucleotide sequence encoding at least one transgene, the first SIR, the second LIR, a second nucleotide sequence encoding at least one transgene, the second SIR, a nucleotide sequence encoding the Rep/RepA of BeYDV, followed by the third LIR.

In some embodiments, the nucleic acid sequence of Rep comprises a sequence with at least 95%, preferably 99%, sequence identity to the complement of nt 859-1522 of bean yellow dwarf virus putative genes V1, V2, C1, C1:C2 (GenBank: Y11023.2). In some embodiments, the nucleic acid sequence RepA comprises the complementary sequence to nt 859-1311 of bean yellow dwarf virus putative genes V1, V2, C1, C1:C2 (GenBank: Y11023.2).

Figure 3A:
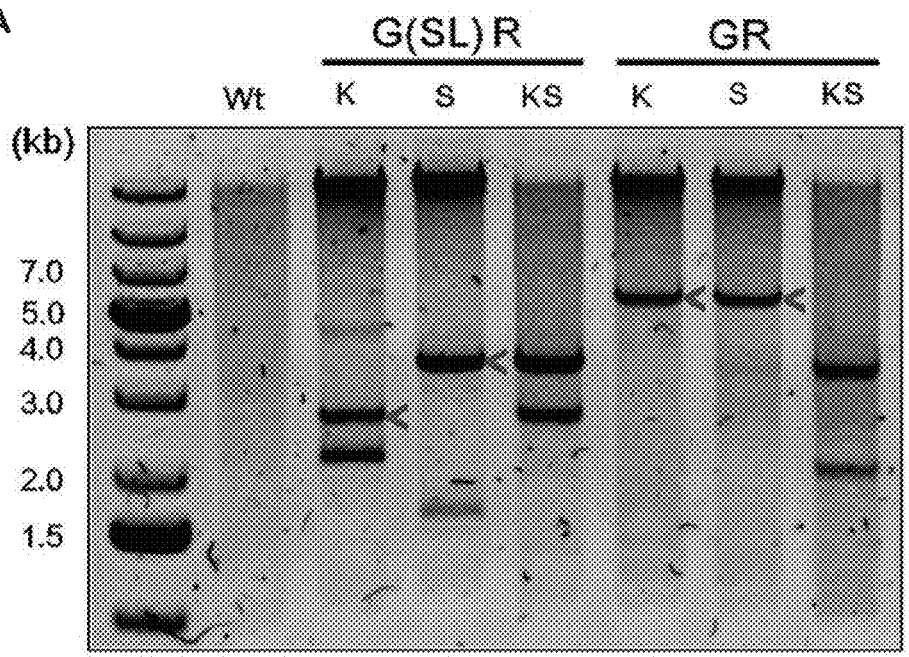
Figure 3B:
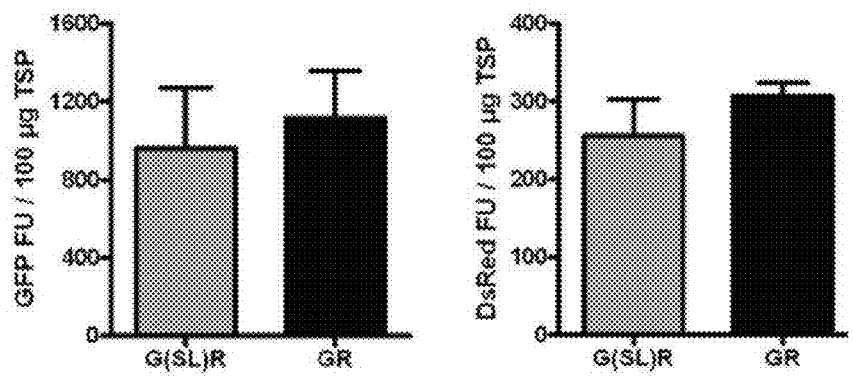

BeYDV requires only two viral cis elements, the LIR and SIR, for replication via the Rep/RepA proteins. This feature, along with the general high fidelity of DNA-based systems, facilitates insertion of large amounts of heterologous genetic information into a BeYDV vector. A notable finding from the current study is that BeYDV replicons can be enlarged as much as 280% of the native viral replicon size without notable detrimental effect on gene expression. Transient infiltration of constructs pBY-GR and pBY-GCR resulted in efficient formation of ~5.4 kb and ~7.1 kb replicons, respectively (FIG. 3). Interestingly, while accumulation of the enlarged replicons was decreased by 38-64% compared to the smaller replicon, the vector pBY-GR resulted in GFP and DsRed expression that was comparable with pBY-G(SL)R (FIG. 3B). Recombinant BeYDV vectors produce more replicons than are needed to achieve maximal expression, and thus reduced replication may be neutral or even beneficial, as the accumulation of excess replicons can enhance cell death (Diamos and Mason, 2018c). Notably, none of the optimized constructs used in this study produced significant cell death by the optimum harvest date. The maximum amount of genetic information that can be placed into a BeYDV replicon vector without compromising the expression level remains to be studied. However, the need to rely on placing multiple expression cassettes into a single large replicon is circumvented by the fact that multiple smaller replicons can be delivered in the same T-DNA vector without any notable loss of efficiency (FIG. 3, FIG. 6). Together, these results highlight the flexibility of the BeYDV system, which can efficiently coexpress multiple proteins in a variety of configurations: e.g. by coinfiltrating multiple T-DNA vectors, by linking multiple individual replicons released from a single T-DNA by the nicking and ligating properties of Rep/RepA, or by arranging multiple expression cassettes in tandem inside of a single large replicon.

By optimizing transgene codons and removing deleterious sequences, improving delivery of the transgene by *Agrobacterium*, modifying vector replication, and improving downstream transcription and translational processes, this system is capable of producing a variety of biopharmaceutical proteins at yields equal to or greater than the highest levels reported in plant-based systems. As shown in the examples, optimizing the genetic elements of the vector enabled simultaneous coexpression of two, three, or four proteins at up to 2.5-fold the expression level of previously known vectors, which are relatively unoptimized (FIGS. 2A-2C and FIG. 5). Many genetic components that can provide a wide range of expression levels in plant systems (Diamos and Mason, 2018a and U.S. patent application Ser. No. 16/976,739).

While using multiple expression cassettes with identical genetic components results in similar production levels of each individual protein, using suboptimal genetic components for some expression cassettes would allow fine-tuning of the expression level of each individual protein subunit. This may be ideal for heteromultimeric proteins that require different ratios of each subunit, or in cases where multiple proteins need to be expressed at low levels (Diamos et al., 2019a and U.S. patent application Ser. No. 17/073,102). In certain embodiments, the optimized BeYDV vectors comprise highly efficient double terminators, which may inhibit induction of silencing signals by RDR6 as well as the P19 suppressor of RNA silencing. While RNA silencing mechanisms may cross-react with expression cassettes containing duplicated genetic elements, no loss of total yield was observed when two, three, or four expression cassettes containing identical 5' and 3' UTRs were coinfiltrated (FIG. 2C).

Figure 2A:
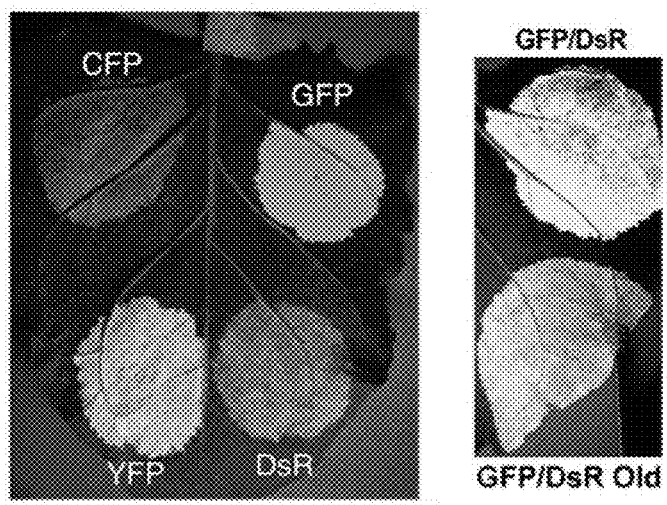
Figure 2B:
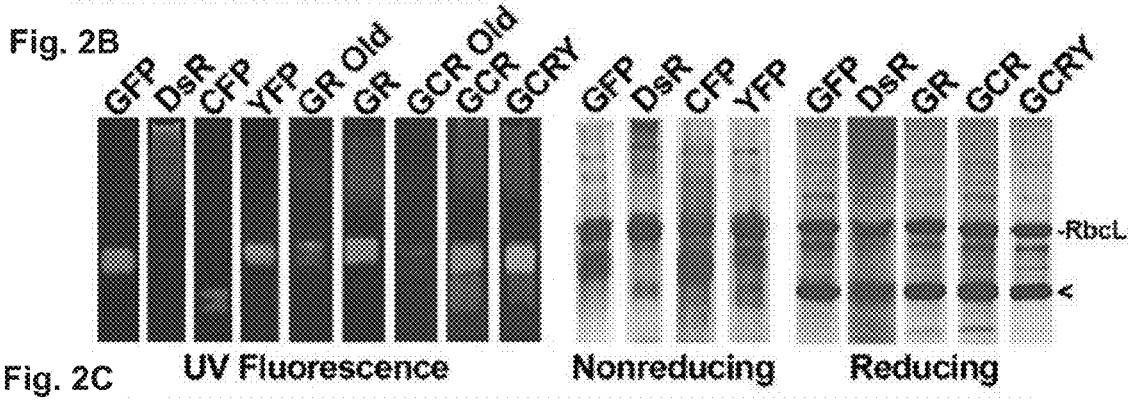
Figure 2C:
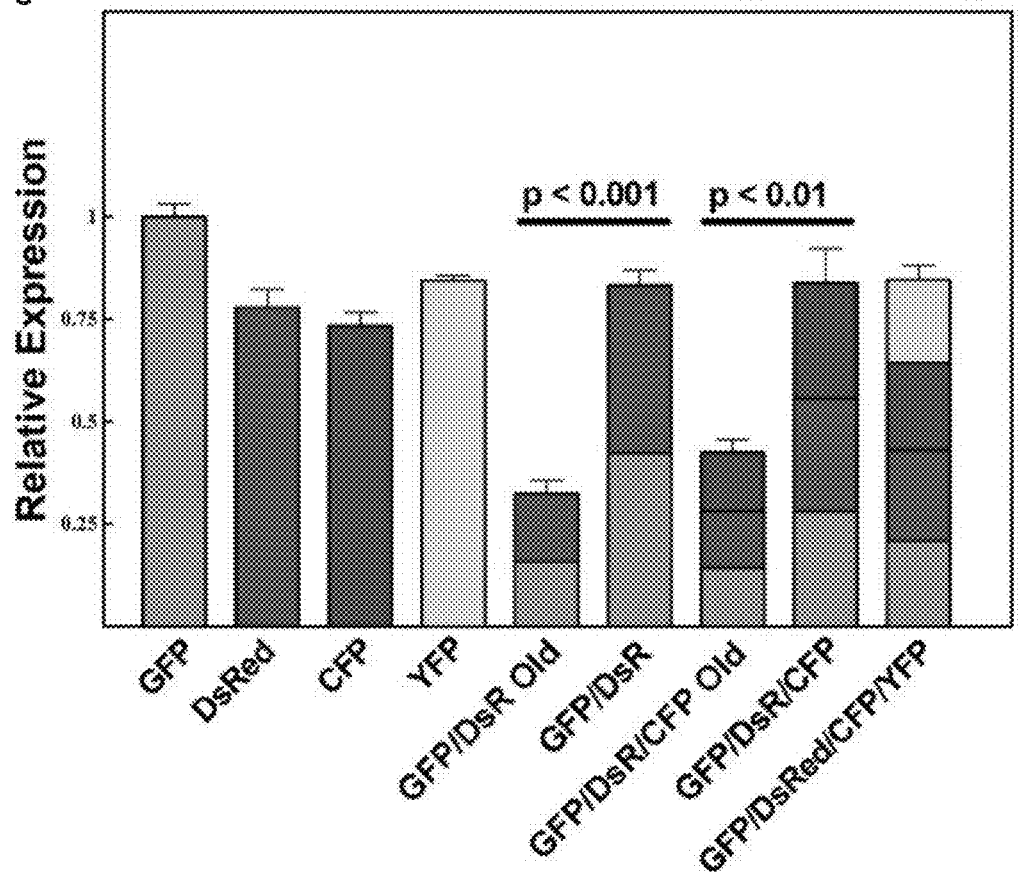

Furthermore, using varied but suboptimal 5' and 3' UTRs clearly negatively impacted expression (FIG. 2C). Since no obvious detriment has yet been observed upon coexpression of additional proteins, it is also possible for these vectors to efficiently produce more than four proteins in the same cell due to the noncompetitive nature of the BeYDV replicons.

Accordingly, the nucleotide sequences encoding the transgenes in the described plant expression system comprises an optimized 5' untranslated region (UTR) and an optimized 3' UTR for each transgene. The optimized 5' UTR comprises the 35S promoter with duplicated enhancer region from cauliflower mosaic virus and a 5' UTR from the psaK gene of *Nicotinana benthamiana*, tobacco mosaic virus, tobacco etch virus, or alfalfa mosaic virus. In some aspects, the 5' UTR from the psaK gene of *N. benthamiana* is truncated. The optimized 3' UTR region comprises at least one element selected from the group consisting of: the tobacco extension terminator with its intron removed, the 3'UTR from the ACT3 gene of *N. benthamiana*, the tobacco Rb7 matrix attachment region, the 3' UTR from the pea rbcS gene, and the 3' UTR from the soybean vspB gene. In some aspects, the tobacco Rb7 matrix attachment region is modified with unwanted restriction enzyme sites removed. In some embodiments, the 3'UTR comprises a double terminator, for example, the 3' UTR comprises the tobacco extension terminator with its intron removed and the 3'UTR from the ACT3 gene of *N. benthamiana*. In certain implementations, the 3' UTR comprises the tobacco extension terminator with its intron removed, the 3'UTR from the ACT3 gene of *N. benthamiana*, and the tobacco Rb7 matrix attachment region. In other embodiments, the 3' UTR comprises the tobacco extension terminator with its intron removed and the tobacco Rb7 matrix attachment region.

In some embodiments, the nucleic acid sequence of TMV spans nt 489-693 of the tobacco mosaic virus isolate TMV-JGL coat protein gene (GenBank: KJ624633.1).

In some embodiments, the nucleic acid sequence of the intronless tobacco extension terminator spans nt 2396-3126 of the complete *N. tabacum* gene for extensin (GenBank D13951.1).

In some embodiments, the nucleic acid sequence of NbACT3 comprises nt 1460-1853 of actin gene (Gene ID Niben101Scf00096g04015.1). In some aspects, where the *N. benthamiana* actin 3' UTR is truncated, the nucleic acid sequence comprises only the downstream 617-nt region of NbACT3 or only the downstream 567-nt region of NbACT3.

In some embodiments, the nucleic acid sequence of the 3' UTR of the pea rbcS gene comprises a sequence that is complementary to the sequence spanning nt 6-648 of transient gene expression vector pUCPMA-M24 (GenBank: KT388099.1). In some aspects, the sequence of rbcS is obtained from pRTL2-GUS (Carrington et al., 1991) by SacI-EcoRI digestion.

In some embodiments, the Rb7 matrix attachment region refers to the sequence of GenBank: U67619.1 or GenBank: KC5555564.1.

In some aspects, a nucleic acid sequence encoding one transgene is between an LIR and its nearest downstream SIR. In other aspects, a nucleic acid sequence encoding two transgenes or three transgenes are between an LIR and its nearest downstream SIR. In such embodiments, each transgene is flanked by an optimized 5' UTR and an optimized 3' UTR. Thus, as shown in FIG. 1, embodiments where the nucleic acid sequence encoding two transgenes are between an LIR and its nearest downstream SIR, the order of the sequences is: the LIR, the 5' UTR of the first transgene, the first transgene sequence, the 3' UTR of the first transgene, the 5'UTR of the second transgene, the second transgene sequence, the 3' UTR of the second transgene, followed by the SIR. Also shown in FIG. 1, embodiments where the nucleic acid sequence encoding three transgenes are between an LIR and its nearest downstream SIR, the order of the sequences in one implement is: the LIR, the 5' UTR of the first transgene, the first transgene sequence, the 3' UTR of the first transgene, the 5'UTR of the second transgene, the second transgene sequence, the 3' UTR of the second transgene, the 5'UTR of the third transgene, the third transgene sequence, the 3' UTR of the third transgene, followed by the SIR.

In certain embodiments, the vector backbone is based on pBY11HA, pBYKEAM, or pBYKEHM. For example, the vector is derived from pBY11HA-GFP (SEQ ID NO. 16), pBYKEAM-BAGFPas6H (SEQ ID NO. 17), or pBYKEHM-Bsa (SEQ ID NO. 18).

In some embodiments, the sequence of the optimized plant expression vector comprises a portion with at least 95% or at least 99% sequence identity to nt 2192-3414 of SEQ ID NO. 16 (an optimized 5'UTR), a portion with at least 95% or at least 99% sequence identity to nt 9615-10751 of SEQ ID NO. 16 (Rep/RepA of BeYDV), and at least one portion with at least 95% or at least 99% sequence identity to nt 4345-5317 of SEQ ID NO. 16 (an optimized 3' UTR) or to nt 7119-9536 of SEQ ID NO. 16 (an optimized 3'UTR).

In some embodiments, the sequence of the optimized plant expression vector comprises a portion with at least 95% or at least 99% sequence identity to nt 2192-3320 of SEQ ID NO. 17 (an optimized 5'UTR), a portion with at least 95% or at least 99% sequence identity to nt 6715-7892 of SEQ ID NO. 17 (Rep/RepA of BeYDV), and at least one portion with at least 95% or at least 99% sequence identity to nt 4219-5735 of SEQ ID NO. 17 (an optimized 3' UTR portion) or to nt 5984-6632 of SEQ ID NO. 17 (an optimized 3'UTR portion).

In some embodiments, the sequence of the optimized plant expression vector comprises a portion with at least 95% or at least 99% sequence identity to nt 2192-3320 of SEQ ID NO. 18 (an optimized 5'UTR), a portion with at least 95% or at least 99% sequence identity to nt 5606-6783 of SEQ ID NO. 18 (Rep/RepA of BeYDV), and at least one portion with at least 95% or at least 99% sequence identity to nt 3414-3714 of SEQ ID NO. 18 (an optimized 3' UTR portion) or to nt 4345-5523 of SEQ ID NO. 18 (an optimized 3'UTR portion).

In particular embodiments, the sequence of an empty optimized plant expression vector (not containing sequences of any transgene for plant expression) comprises a portion with at least 95% or at least 99% sequence identity to nt 1-3424 of SEQ ID NOS. 16-18 and a portion with at least 95% or at least 99% sequence identity to nt 4247-14211 of SEQ ID NOS. 17 and 18 or nt 7107-17111 of SEQ ID NO. 16.

The described plant expression system are suitable for producing multimeric proteins, such as antibodies, from a single vector. Another exemplary benefit of the optimized plant expression system include shortened time of production. This streamlined system requires only 4-5 days from the delivery of the transgene to the harvesting of plant material that contains the desired protein. The optimized BeYDV vectors also offer advantages over expression systems based on RNA viruses. While RNA-based systems need to use multiple non-competing viruses to express separate proteins in the same cell, BeYDV vectors are noncompeting and can be used to produce heteromultimeric proteins from a single vector. Finally, the large host range of BeYDV allows high level protein production in a variety of dicot plants.

Exemplary Monoclonal Antibodies Produced Using the Described Plant Expression Vectors In recent years, monoclonal antibodies have been widely explored for use in immunotherapies and treatments for infectious diseases. One active area of research in antibody development focuses on the production of therapeutic mAbs against flaviviruses. The Flaviviridae family contains over 53 viruses, including many major health pathogens such as Dengue virus, yellow fever virus, West Nile virus, Japanese encephalitis virus, and ZIKV which create a significant global public health burden. For Dengue alone, it is estimated that there are over 390 million cases annually. An ideal mAb therapeutic against flaviviruses would: 1) be able to recognize and effectively neutralize multiple types of viruses; 2) be produced in an economical and cost-effective manner; and 3) be able to be easily purified. The antibody 2A10G6 recognizes an epitope in the highly conserved fusion loop found on the flavivirus envelope protein, allowing it to effectively neutralize infection of all four Dengue serotypes, yellow fever, and West Nile virus. 2A10G6 has also been shown to bind to and neutralize the Zika E protein.

Unfortunately, the 2A10G6 antibody is murine. As such, direct delivery of this antibody to humans could result in an unwanted immune response to the antibody and result in swift clearance from circulation. One way of circumventing this problem is to create a humanized, chimeric version of the antibody in which the murine heavy and light chains are genetically fused into a human antibody. This type of antibody engineering has been studied since the 80s with great success leading to many marketed mAb treatments. Here, a more humanized 2A10G6 antibody for expression in *N. benthamiana* is described. The chimeric antibody reached high levels of expression that exceeded the level that is considered to be commercially viable for plant-made antibodies (Nandi et al., 2016). Furthermore, the plant-produced antibody was correctly assembled, purified to >95% homogeneity by a simple one-step purification process, and retained its ability to bind to Zika envelope protein with potent neutralizing activity, similar to the native murine antibody (FIGS. 7B, 7C, and 8A).

To further demonstrate the general effectiveness of the BeYDV plant expression system, two other mAbs were produced. The anti-Ebola GP1 mAb 6D8 was produced using an unoptimized BeYDV vector (Huang et al., 2010) and thus served as a benchmark to compare updated vector configurations for mAb production. New optimized vectors (FIG. 1) provided an approximate 4-5-fold increase in yield compared to the old unoptimized vectors (FIG. 5), allowing milligram quantities of mAb to be produced from a single plant leaf. While previous vector iterations caused plant cell toxicity (Diamos and Mason, 2018c), no cell death was observed for c2A10G6 (FIG. 8A) or any of the other mAbs used in this study. Though this mAb yield is high, the relatively higher expression of the fluorescent proteins indicates that there are still inefficiencies for mAb production. Protein engineering has been used to remove certain motifs in mAb structure that are susceptible to degradation or instability in plants, allowing mAb production as high as 2 g/kg LFW.

Analysis of the chimeric antibody showed that it was efficiently expressed in plants at 1.5 grams of antibody/kilogram of leaf tissue, can be purified to near homogeneity by a simple one-step purification process, retains its ability to recognize the Zika virus envelope protein, and potently neutralizes Zika virus. Two other monoclonal antibodies were produced at similar levels (1.2-1.4 g/kg). Using these optimized vectors, milligram quantities of three different mAbs can be produced from a single plant leaf. Accordingly, also described herein are methods for producing in plants a chimeric antibody, for example, a chimeric antibody against a highly conserved fusion loop epitope found on flaviviruses. Notably, the plant-expressed antibodies producing according to the methods and expression systems described herein are correctly assembled, can be purified to near-homogeneity with a simple purification procedure, and retains the binding ability of the original murine antibody.

Illustrative, Non-Limiting Example in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

1. Simultaneous Coexpression of Two Fluorescent Proteins Using Optimized BeYDV Vectors Two proteins have been efficiently and simultaneously produced by either a single replicating BeYDV vector or by multiple codelivered vectors (Huang et al., 2010). In order to study the coexpression of multiple genes, an optimized vector was created by the following method: the coding sequences for GFP and DsRed were incorporated into vectors containing a single BeYDV replicon, the NbPsaK 5' UTR, a double terminator consisting of the intronless tobacco extensin terminator fused to the NbACT3 3' UTR, and the Rb7 matrix attachment region (FIG. 1) (Diamos et al., 2016; Diamos and Mason, 2018c, 2018a). These vectors were named either "pBYKEAM" (signifying that it contained one expression cassette) or "pBYKEAM2" (signifying that it contained two expression cassettes). The original vector without the optimized components (Huang et al., 2010) (referred to as pBY-GR in this study) was agroinfiltrated into the leaves of N. benthamiana along with optimized vectors expressing GFP or DsRed either alone or coinfiltrated together. While the unoptimized vector produced weak yellow fluorescence typical of GFP and DsRed expressed together, the optimized vector produced bright yellow fluorescence (FIG. 2A). Protein extracts from agroinfiltrated leaf spots were analyzed by SDS-PAGE under UV light or after staining with Coomassie Brilliant Blue.

Under nonreducing conditions, the ~27 kDa GFP is typically visible as an approximately dimer-sized fluorescent band. In contrast, the ~26 kDa DsRed runs as a very diffuse high molecular weight fluorescent band (FIG. 2B, compare lanes "GFP" and "DsRed"). The optimized vector produced notably increased levels of fluorescence of both GFP and DsRed compared to the old, unoptimized vector (FIG. 2B, compare lanes "GR old" to "GR"). To more accurately assess the difference in expression, reducing SDS-PAGE conditions were used to collapse the higher molecular weight bands into a single monomeric-sized band. Quantifying the band intensity revealed that the optimized vector produced 2.54-fold ($p<0.001$) more GFP and DsRed than the original vector. The yield of GFP and DsRed was up to 50% of the plant total soluble protein or 3-5 g recombinant protein per kilogram leaf fresh weight (g/kg LFW) (FIG. 2B, reducing lanes).

Although the fluorescence intensity of each protein may not correlate directly with yield due to differences in their peak fluorescence, it is possible to compare the relative fluorescence of the same protein expressed either alone or coexpressed. Using samples taken from constructs GFP, DsRed, and GR each agroinfiltrated nearby on the same leaves to reduce variability, the band intensity of GFP expressed by itself to the GFP band intensity in construct GR was compared, revealing a 52%±4 decrease in GFP fluorescence. Similar results were found when comparing DsRed alone to construct GR. Therefore, the data suggests construct "GR" produces roughly half as much GFP and DsRed as each construct expressed alone. Since the total yield of recombinant protein is nearly equal between either GFP or DsRed alone and construct GR (FIG. 2B, reducing lanes, compare "GFP" and "DsR" to "GR"), roughly equal levels of GFP and DsRed are made in construct GR (FIG. 2C, colored to indicate the relative expression of each construct).

Because BeYDV replicons can be arranged either as individual tandem replicons that are separately released and replicated, or as a single large replicon containing multiple expression cassettes, the different configurations were tested whether one configuration of viral replicons was more optimal than the other for expression of multiple proteins. A single replicon containing GFP and DsRed expression cassettes was compared to a vector containing GFP and DsRed in separate replicons. In either case, no significant differences in expression were observed, so both configurations were efficiently replicated (FIGS. 3A and B).

2. Simultaneous Coexpression of Up to Four Fluorescent Proteins

Figure 3C:
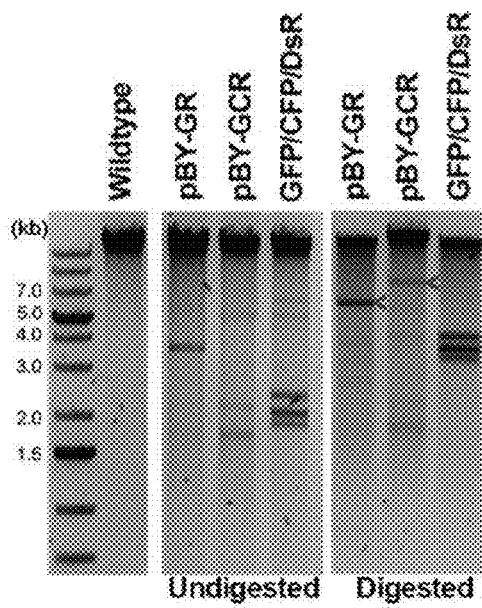
Figure 4:
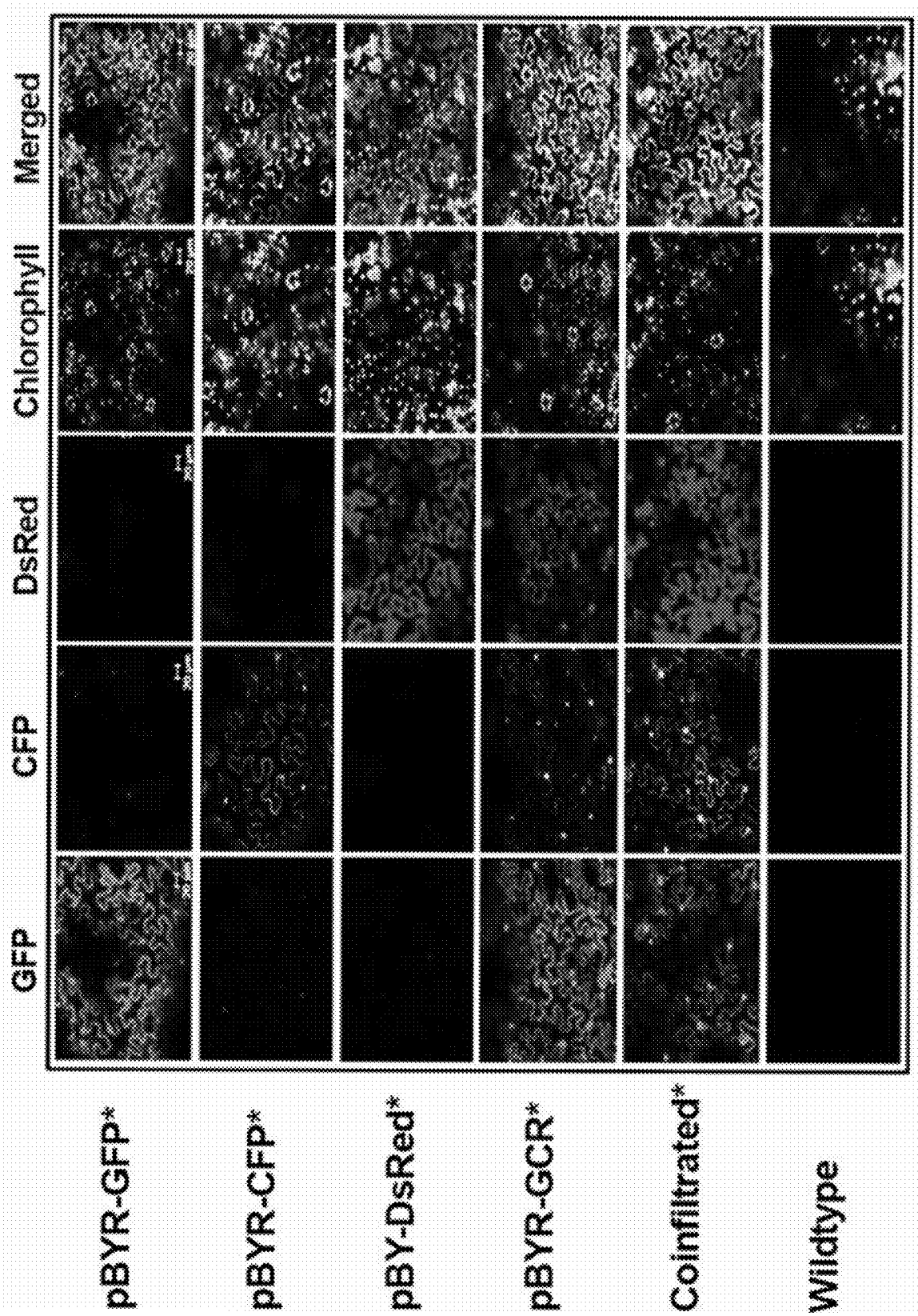

To study the effects of expressing three proteins simultaneously, BeYDV replicon vectors were created with expression cassettes for GFP, DsRed, and CFP. The vector pBYGCR (FIG. 1) was designed to contain varied 5' UTRs and 3' UTRs to test whether unwanted recombination or RNA silencing might result from repeated genetic elements. Alternatively, individual expression cassettes for GFP, DsRed, and CFP which contained identical optimized vector components were coinfiltrated. By nonreducing SDS-PAGE, CFP runs slightly below GFP despite its similar monomeric size of ~26 kDa, allowing the fluorescence of each protein to be observed independently. The optimized vector produced a substantial increase of all three fluorescent proteins compared to the unoptimized vector, indicating that if there is a detrimental effect of repeated genetic elements, it is outweighed by the benefit gained from using optimized genetic elements (FIG. 2B-C, compare "GCR old" to "GCR"). Producing three proteins simultaneously resulted in the same total yield of recombinant protein (FIG. 2B, reducing lanes). (FIG. 2B, lane "GCR"). An analysis of replicon formation revealed that the single large replicon displayed somewhat reduced replication, however high accumulation of replicons was still observed in all constructs (FIG. 3C). Confocal microscopic examination revealed colocalized green, cyan, and red fluorescence, indicating efficient simultaneous expression of the three different proteins in each cell. In contrast, leaf samples individually infiltrated with GFP, DsRed, or CFP alone showed only a single fluorescent signal (FIG. 4).

Finally, to test simultaneous expression of four proteins, an optimized YFP vector was coinfiltrated with optimized GFP, DsRed, and CFP vectors. The ~26 kDa YFP runs at a similar size to GFP on non-reducing SDS-PAGE but is yellowish/green in appearance under UV illumination. The sample containing all four proteins had slightly reduced DsRed/CFP fluorescence, but an increased green/yellow fluorescence, likely due to the combined GFP/YFP bands overlapping (FIG. 2B, lane GCRY). Compared to coexpression of three proteins, the total recombinant protein yield was not significantly reduced when all four proteins were coexpressed (FIG. 2B, reducing lanes and FIG. 2C). These data suggest that optimized BeYDV vectors can produce high levels of up to 4 proteins simultaneously.

3. Expression of mAbs Using Optimized Plant Expression Vectors

Three mAbs were chosen for expression using optimized BeYDV vectors. We have previously described production of the humanized 6D8 (6D8), an IgG1 targeting the Ebola virus glycoprotein GP1 (Huang et al., 2010). The antibody 2A10G6 recognizes an epitope in the highly conserved fusion loop on the flavivirus envelope protein, allowing it to effectively neutralize a wide range of flaviviruses. To create a more humanized form of 2A10G6, the variable regions in 6D8 were replaced with the variable regions from 2A10G6 (referred to as chimeric 2A10G6 or c2A10G6). Lastly, we also produced the mAb HSV8, a human-derived antibody which neutralizes herpes simplex virus (HSV) in mice and traps HSV in human cervicovaginal mucus. Optimized BeYDV vectors containing the plant codon-optimized c2A10G6, 6D8, and HSV8 heavy and light chain coding sequences were agroinfiltrated into glycoengineered *N. benthamiana* that produces highly homogenous mammalian-like glycans. Since the antibodies described in this study have potential as human therapeutics, it was important to use an expression host capable of creating antibodies that contain a mammalian-like glycosylation pattern. To maintain consistency, only glycoengineered plants were used for the antibody expression experiments. Then, antibody production from the leaves were quantified using ELISA designed to detect fully assembled IgG. Using an unoptimized vector (Huang et al., 2010), 6D8 was produced at a level of 0.38 mg/g LFW while the optimized vectors produced 1.21 mg/g LFW 6D8, 1.42 mg/g LFW HSV8, and 1.47 mg/g LFW 2A10G6 (FIG. 5). To determine whether replicon configuration affects IgG production, vectors containing the expression cassettes for the 6D8 heavy and light chains were either placed in a large single replicon (pBY-HL) or individual smaller replicons (pBY-H(SL)L). In agreement with our results using GFP and DsRed, no differences in expression were observed between the configurations, indicating the flexibility of BeYDV replicons in coexpressing multiple proteins (FIG. 6).

4. Characterization and Purification of Chimeric 2A10G6

Optimized vectors contain components designed to reduce cell death (Diamos et al., 2016; Diamos and Mason, 2018c). As c2A10G6 had not been previously made in plants, leaves infiltrated with c2A10G6 were analyzed at 4 DPI for signs of chlorosis or necrosis which would suggest that the construct was toxic to the plant. However, there was no visible necrosis and faint chlorosis, indicating that antibody accumulation in the leaves was well tolerated (FIG. 7A). To test whether the antibody was correctly assembled, clarified protein extracts from leaf samples were separated by SDS-PAGE. On both Coomassie-stained gel and western blot, a prominent band at the fully assembled heterotetrameric size of ~150 kDa was visible in the samples agroinfiltrated with c2A10G6 but not in the uninfiltrated control (FIGS. 7B and 7C). This further confirmed the high level of expression since the antibody band was prominent in a clarified plant extract, even before purification. The clarified leaf samples were then assessed by acid precipitation to verify if the antibody was stable after exposure to low pH conditions. Since acid precipitation removes plant contaminants that could otherwise hinder purification, it is a useful method to enrich leaf extract containing antibodies. Samples of clarified plant extract were briefly exposed to low pH conditions (~pH 4.1), then raised back to a neutral pH. Upon acid precipitation, several plant contaminant bands were removed, including the abundant rubisco large subunit band (~63 kDa), resulting in substantial enrichment of the antibody (FIG. 7B). After purification by protein G affinity chromatography, samples assessed under non-reducing and reducing conditions on both a silver-stained gel and a stain-free gel show that the samples were highly pure (>95%) with very little degradation (FIG. 7D).

5. c2A10G6 Recognition of the Fusion Loop Epitope

Figure 8B:
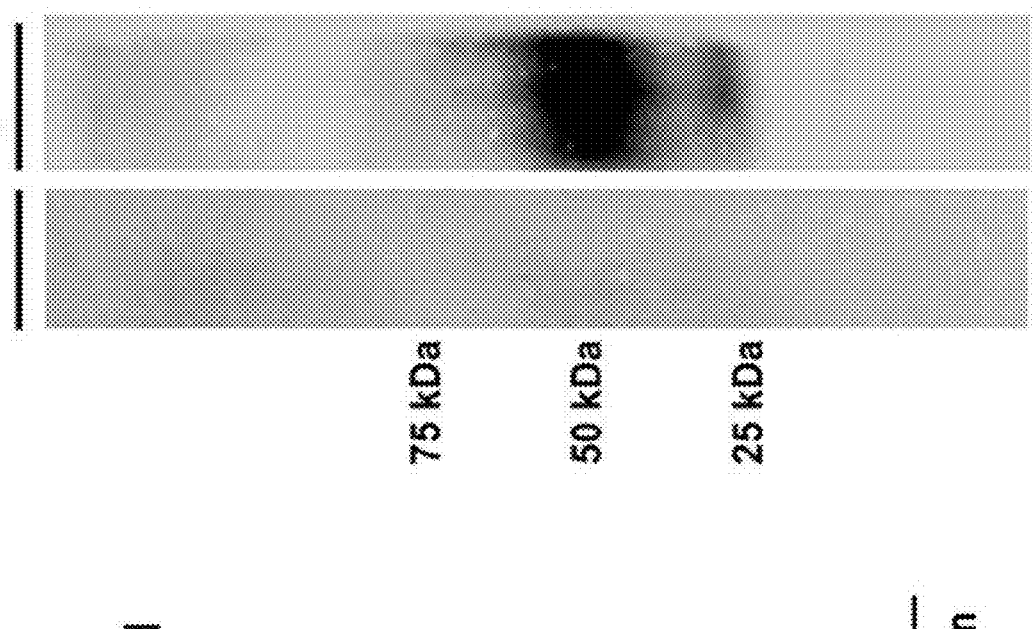
Figure 8A:
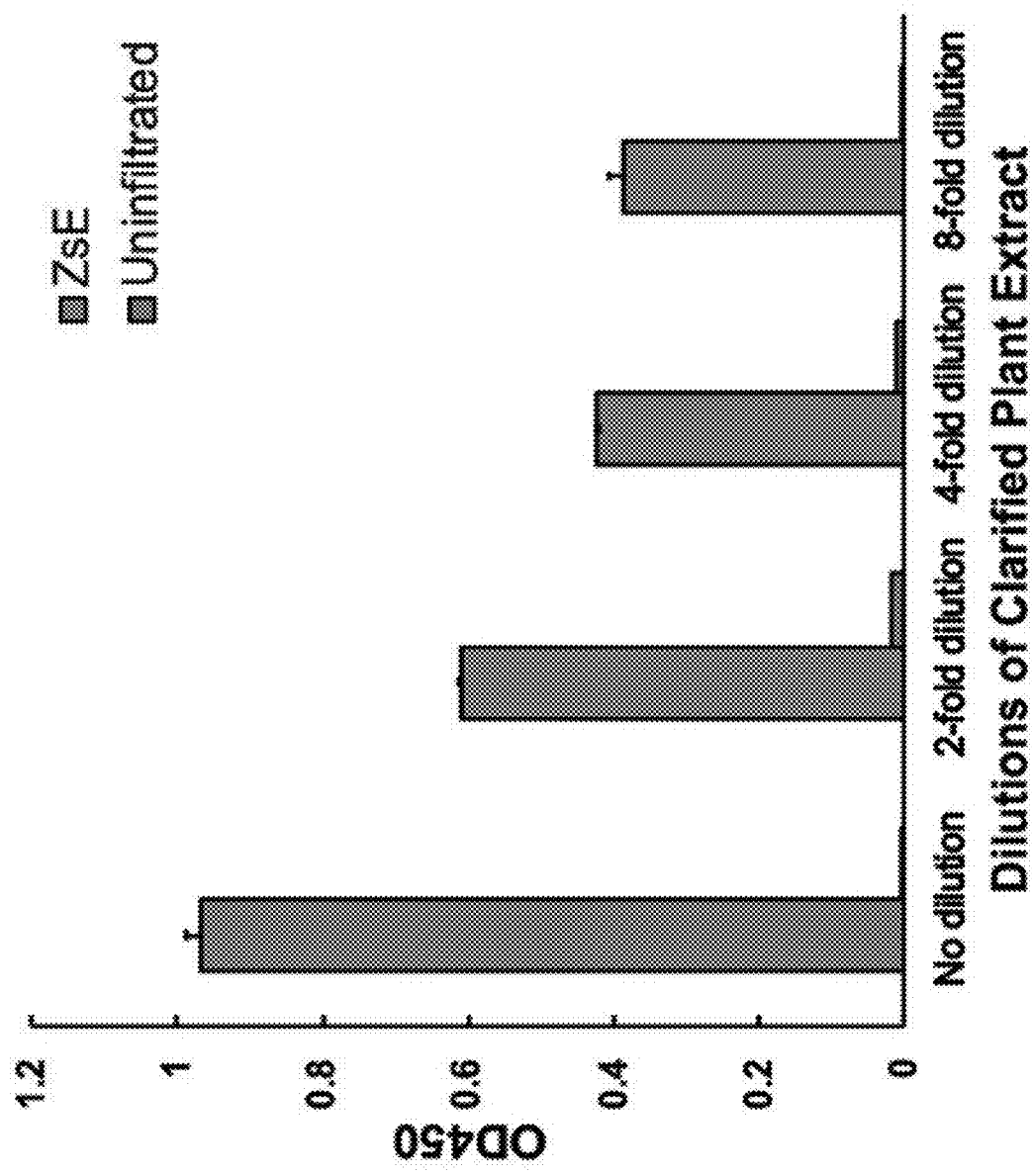
Figure 9:
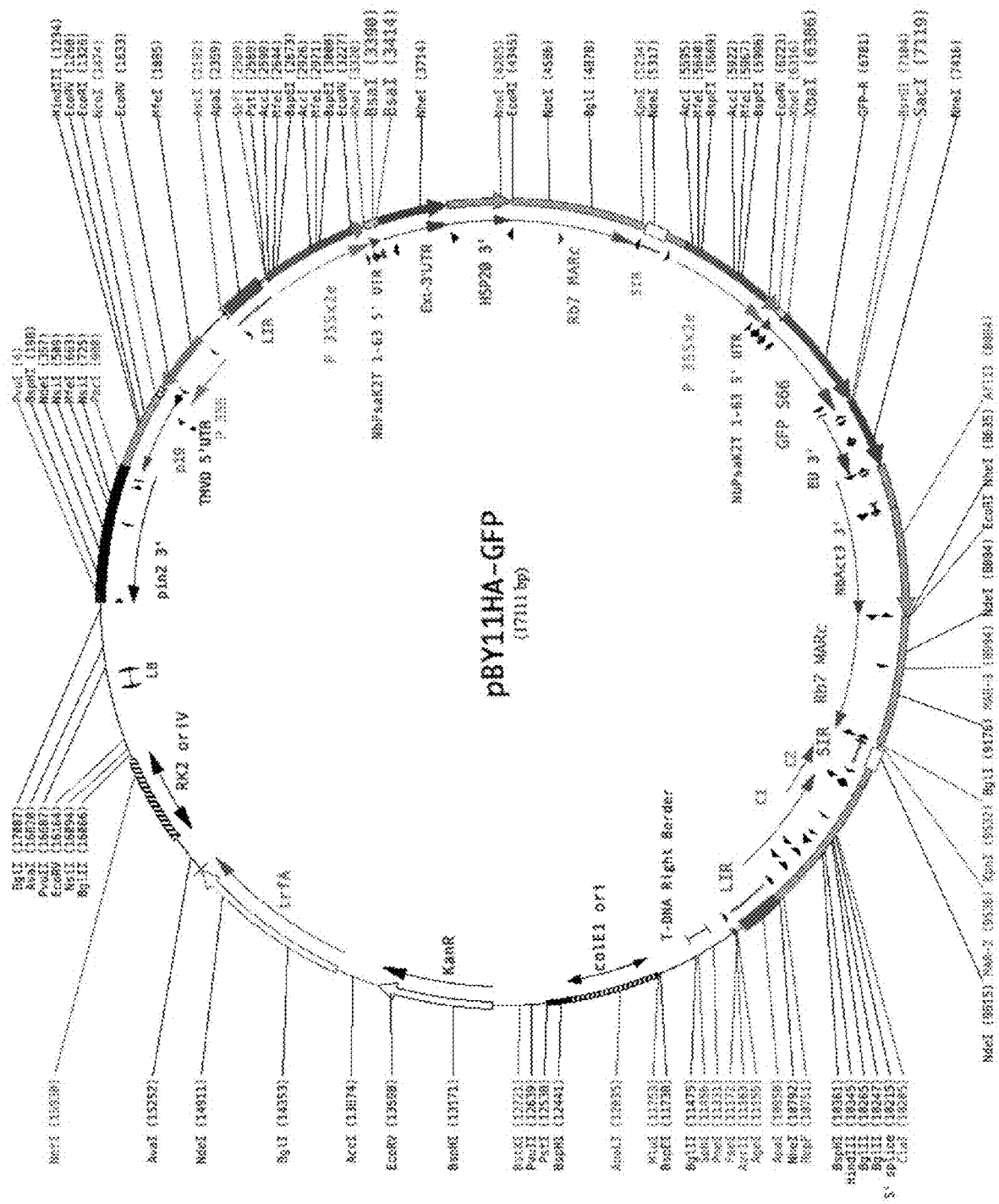
Figure 10:
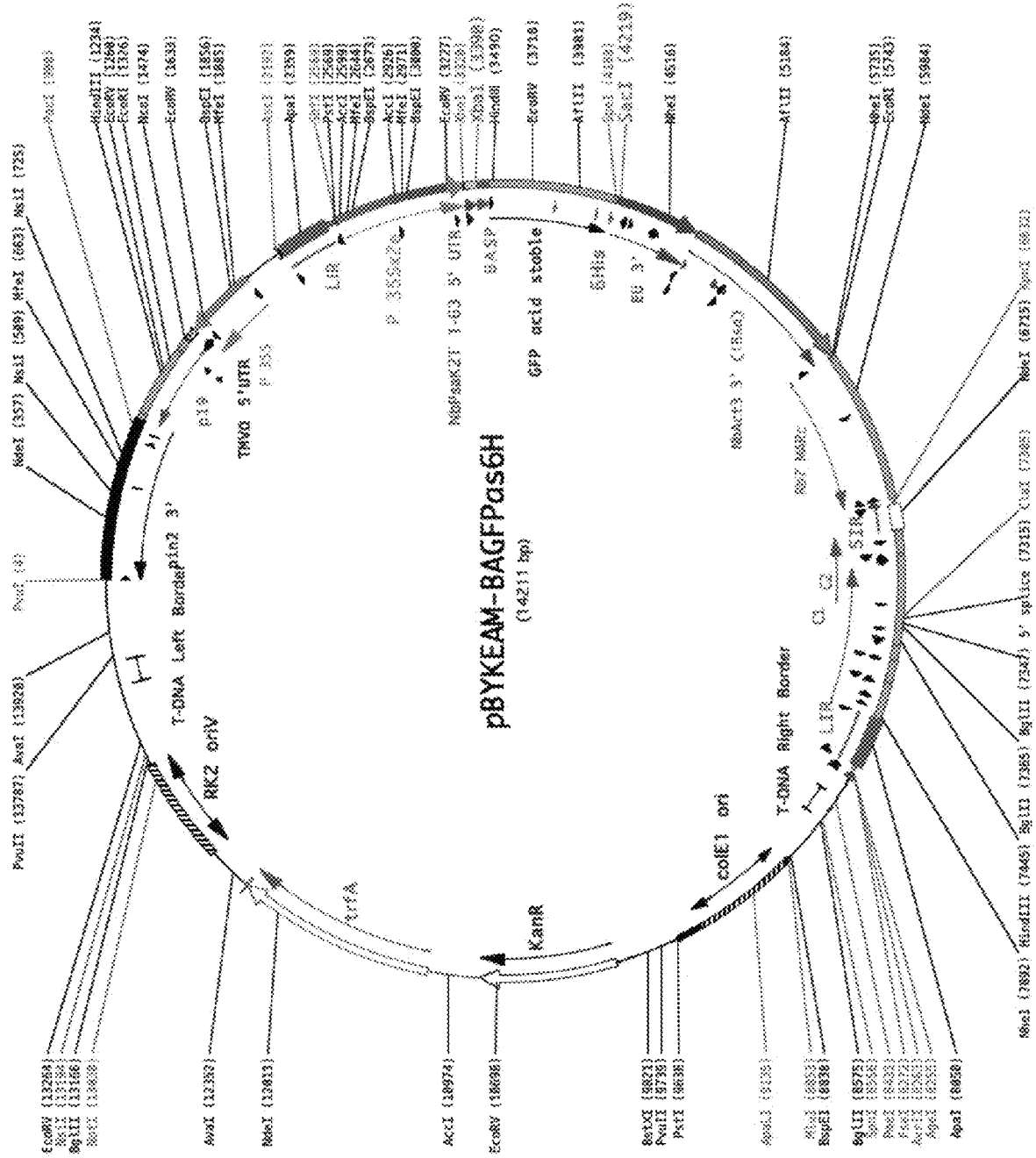
FIG. 10 depicts the map of pBYKEAM-BAGFPas6H (sequence set forth in SEQ ID NO. 17).
Figure 11:
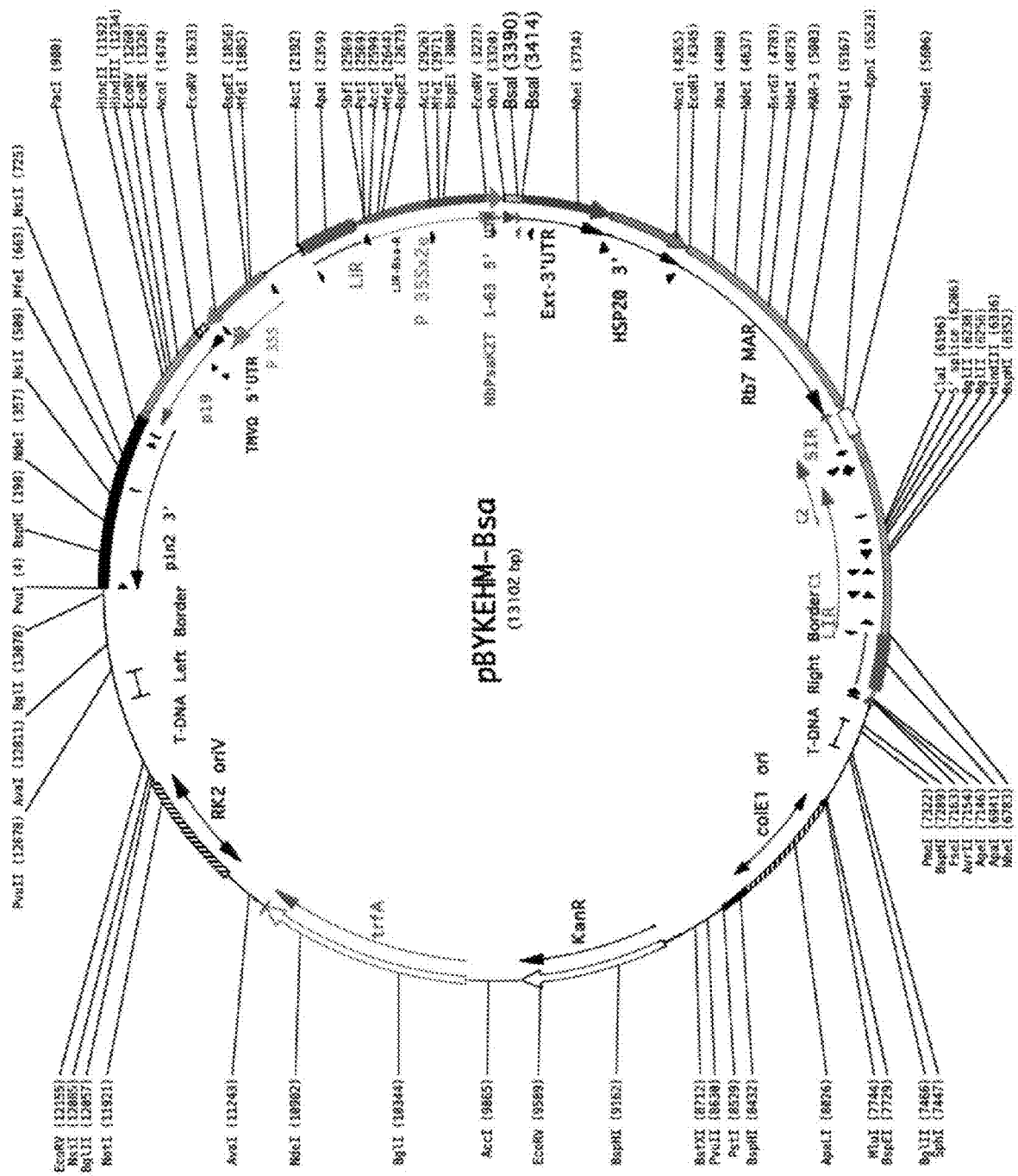
FIG. 11 depicts the map of pBYKEHM-Bsa (sequence set forth in SEQ ID NO. 18).

Since c2A10G6 is a chimeric version of the murine mAb 2A10G6 that recognizes a highly conserved fusion loop on ZIKV, it was necessary to verify that the chimeric version retains the ability to recognize and bind the fusion loop epitope. First, the soluble ectodomain of the Zika envelope protein (ZsE, amino acids 1-403) that contains the fusion loop was expressed in plants. Next, a direct ELISA was conducted in which a clarified ZsE plant extract was directly bound to a 96 well high-binding polystyrene plate and probed with serial dilutions of purified c2A10G6. Uninfiltrated leaf extract was also included in the experiment to ensure there was no cross-reactivity with native plant proteins. As shown in FIG. 8A, the chimeric antibody recognized the Zika soluble envelope while having negligible reactivity with native plant proteins. As an additional test, Zika prME was also expressed in plants and probed via western blot with c2A10G6. The antibody reacted with the prME containing extract but not an uninfiltrated leaf extract (FIG. 8B). Together, these data show that the chimeric antibody retains its ability to bind the Zika envelope protein.

6. Materials and Methods

A. Expression Vector Construction

The construction of plasmids pBYGFP and pBYDsRed has been previously described (Huang et al., 2010). For the construction of pBYCFP, the CFP gene (Accession number EU530627) was PCR amplified from plasmid pIBT-PR7: eCFP (a kind gift from Dr. Z. Huang) with primers GFP-BsaF and GFP-PacI, digested with BsaI and PacI, and ligated with pBYR7, a derivative of pBYR2 (Chen et al., 2011). The CFP cassette was obtained by PCR with primers U35S-SpeF and Ext6-SalR using pBYCFP as a template, digested with SpeI-SalI, and ligated with pBY-GR digested SpeI-SalI, to yield the single-replicon three-expression cassette vector pBY-GCR. An optimized BeYDV expression vector for GFP was created by three fragment ligation: the backbone vector pBYR2e-MRtxGM (Diamos et al., 2016) was obtained by XhoI-KpnI digestion; the Rb7 MAR was also obtained from pBYR2e-MRtxGM by KpnI-EcoRI digestion; a fragment containing the PsaK2 5' UTR, GFP, tobacco extension intronless 3' UTR, and NbACT 3' UTR was obtained from pPS-OGFPM-EA (Diamos and Mason, 2018a) by XhoI-EcoRI digestion. The resulting vector, pBYKEAM-GFP, was used to create individual expression vectors for DsRed, CFP, and YFP by a three-fragment ligation: the backbone from pBYKEAM-GFP was obtained by XhoI-AgeI digestion; the Rep/MAR genes were obtained by AgeI-SacI digestion; and DsRed/CFP/YFP were obtained by XhoI-SacI digestion of pBYDsRed/pBYCFP/pBYYFP (gifts from Z. Huang, Arizona State University).

BeYDV-based tandem dual replicon constructs. pBYGFPDsRed.R was described previously (Huang et al., 2010) and renamed as pBY-G(SL)R in this study. Construct pBY-GR was designed to contain two expression cassettes in tandem and to be flanked by LIR and SIR. For the construction of pBY-GR. Primer sets GR5-1/GR5-2 9 and GR3-1/GR3-2 were used for initial amplification in separate PCR reactions using pBY-G(SL)R as a template. The resulting PCR fragments were mixed and amplified using primers GR5-1 and GR3-2, complementary to the ends of the two initial fragments. The resulting PCR product was digested with SacI-KpnI and ligated with pBY-G(SL)R digested with SacI-KpnI, to yield pBY-GR.

Dual cassette single replicon vectors. pBYKEMd2 (FIG. 1) is based upon pBYR11eMa-h6D8-L2 (Diamos et al., 2019b) and contains the optimized PsaK2 5' UTR, tobacco extensin terminator, and Rb7 MAR (Diamos et al., 2016). The first cassette contains BsaI sites in inverted orientations in order to permit insertion of a coding sequence between PsaK2 5' UTR and Ext 3', and the second cassette enables insertion of a coding sequence between unique XbaI and SacI sites (FIG. 1). The insertion of the NbACT 3' UTR (Diamos and Mason, 2018a) downstream of the Ext 3' in pBYKEMd2 produced pBYKEAM2, having double terminator cassettes.

mAb 2A10G6 and Zika antigen cloning. The amino acid sequences of the murine heavy and light chain variable regions (VH and VL) of anti-Zika virus mAb 2A10G6 were obtained from the NCBI Protein Databank (5JHL_H and 5JHL_L). The VH and VL amino acid sequences were codon-optimized for expression in N. benthamiana plants (Geyer et al., 2010), and the nucleotide sequences were synthesized as gBlocks® Gene Fragments (Integrated DNA Technologies). PCR of the plasmid pBYR9-K3 was conducted with primers 6D8 CL-F and Ext3i-R to copy the human light chain constant region (CL) from humanized mAb 6D8 anti-Ebola antibody (Huang et al., 2010). The VL and CL fragments were fused by overlapping PCR, and the resulting fragment was digested with XbaI and SacI for insertion into pBYKEMd2 (FIG. 1), to create pBYKEMd2-5JHL-K. The murine VH gene block digested with XhoI and NheI and fused with the humanized heavy chain human CH region (Huang et al., 2010). The dual cassette vector containing both H and L chains was created by insertion of the chimeric VH-CH segment into the BsaI sites of pBYKEMd2-5JHL-K.

Zika virus antigens were produced to test mAb binding. The coding DNA sequence of ZIKV structural proteins (GenBank accession AMC13911) was synthesized with codons optimized for N. benthamiana (idtdna.com). Zika soluble ectodomain (amino acids 1-403), here called ZsE, was fused via the C-terminus to a 6H tag was created by ligating two DNA fragments: (1) pBYe3R2K2Mc-L2(14-122) (Diamos et al., 2019b) was digested XhoI-SpeI; (2) the Zike E soluble ectodomain was digested XhoI-SpeI. The resulting vector is pBYe3R2K2Mc-BAZsE6H. ZIKV prM, M, and E protein (prME) was obtained by PCR on template pUC57-ZCME-F (a kind gift from Lydia Meador) with primers ZprMBsaF and M13RHT, creating BsaI and SacI sites. To amplify a segment containing the barley alpha amylase signal peptide (BASP), PCR was performed on pBYR2eK2M-BAZE with primers 35S-F and BASP-G-Bsa-R. The purified PCR products for ZprME and BASP were digested with BsaI-SacI and BsaI-XhoI, respectively. The backbone vector pBYR2eK2MC-GFP (Diamos and Mason, 2019) was digested with SacI-XhoI and ligated with the PCR products to make pBYR2e3K2M-BAZprME (referred to in the text as ZprME).

mAb HSV8 cloning. The anti-herpes simplex virus human mAb HSV8 H and L chain coding sequences were a kind gift of Larry Zeitlin (MAPP Biopharmaceutical, San Diego, CA). The VL and VH coding segments were fused to the mAb 6D38 CL and CH coding segments, respectively, as described above for mAb 2A10G6. The L sequence was inserted into pBYKEMd2 (FIG. 1) via XbaI-SacI, followed by H sequence insertion via BsaI-BsaI, to produce pBYKEMd2-HSV8.

TABLE 1

Oligonucleotides used

| Primer | Sequence | SEQ ID NO. |
|---|---|---|
| GR5-1 | GCGGTACCCAATTCGCCCTATAGTGAGTCG | 1 |
| GR5-2 | GTGTCGTGCTCCACCATGCCGTCGACGCACTAG TCGATAGCTTGATGCATGTTGTC | 2 |
| GR3-1 | GACAACATGCATCAAGCTATCGACTAGTGCGTC GACGGCATGGTGGAGCACGACAC | 3 |
| GR3-2 | GAGAGCTCCACCGCGGTGGC | 4 |
| U35S-Spe-F | GGACTAGTGACCCTCCTGCAGGTCAAC | 5 |
| Ext3-Sal-R | GCGTCGACCGAAACTGAACAAAACATACAC | 6 |
| ZprM-Bsa-F | gGGGTCTCTCgTGGTGCCGAGGTCACTAGAC | 7 |
| M13-RHT | GGAAACAGCTATGACCATG | 8 |
| 35S-F | AATCCCACTATCCTTCGC | 9 |
| BASP-G-BSA-R | gcGGTCTCCACCAGAAGCAAGAGAAGC | 10 |
| GFP-Bsa-F | aggGGTCTCgTGGTatggtgagcaagggcga | 11 |
| 5'-GFP-PacI | gcgttaattaaaccaccatggtgagcaagggcg aggagc | 12 |
| Ext6-SalR | GCgtcgacCGAAACTGAACAAAACATACAC | 13 |
| 6D8-CL-F | CCATCTGTCTTCATCTTtCCt | 14 |
| Ext3i-R | CAATTTGCTTTGCATTCTTGAC | 15 |

B. Protein Production, Extraction, and Purification

Agrobacterium tumefaciens strain EHA105 was transfected with expression vectors via electroporation. Resulting strains were confirmed using PCR and restriction digestion of purified plasmids. Confirmed Agrobacterium strains were grown overnight at ~30° C. in YENB media+50 mg/L kanamycin and 2.5 mg/L rifampicin. Agrobacterium was pelleted for 10 min at 5,000 g. The pellets were resuspended in infiltration buffer [10 mM 2-(N-morpholino) ethanesulfonic acid (MES), pH 5.5 and 10 mM MgSO4) to a final OD600 of 0.2 for single vector infiltrations. For multi-vector infiltration experiments, Agrobacterium were mixed such that the final OD600 of each vector was equal to 0.2. Agrobacterium suspensions were infiltrated using a syringe without needle into the leaves of 5-6 week old glycoengineered N. benthamiana silenced for production of the plant-specific β1,2-linked xylose and α1,3-linked (Castilho and Steinkellner, 2012). Infiltrated leaves were harvested 4 days post infiltrations (DPI) unless otherwise noted.

0.1-gram samples of leaf tissue expressing fluorescent protein were homogenized in 1:5 w/v extraction buffer (25 mM Tris-HCL, 125 mM NaCl, 3 mM EDTA, pH 8.0 with 50 mM sodium ascorbate, and 2 mM phenylmethylsulfonyl fluoride (PMSF) added before extraction). The homogenization process was conducted as follows: 12-14 ZnO beads, 2.0 mm, (Fisher Scientific, Waltham, MA, United States) were added to tubes containing leaf samples and extraction buffer. The tubes were bead beaten using a Bullet Blender machine (Next Advance, Averill Park, NY, United States) for two 5-minute rounds. Homogenized leaf tissue was then rotated at room temperature or at 4° C. for 10-15 min. The samples were spun down at 13,000 g for 10-20 min at 4° C. in a 5417R centrifuge (Eppendorf, Hauppauge, NY, United States) and the supernatant transferred to a new tube. The samples were recentrifuged at 13,000 g for 10-20 min at 4° C. to obtain a clarified extract free of major plant contaminants.

For small-scale antibody experiments, 0.05-gram leaf samples were collected at 5 DPI. The samples were then homogenized in ice-cold, 1:5 w/v extraction buffer at pH 8.02 (25 mM Tris-HCl, 125 mM NaCl, 3 mM EDTA, 0.1% Triton X-100, 50 mM sodium ascorbate, and 2 mM PMSF). Homogenized leaf extracts were rotated at 4° C. for 18 minutes, then centrifuged at 13,000 g for 12 minutes. Following the centrifugation, the supernatants were transferred to new tubes for further analysis. An acid precipitation of the samples was conducted by adding 1N phosphoric acid so that the final acid volume was 4% of the soluble leaf extract (~pH 4.1). Following a brief centrifugation at 13,000 g for 2 min, the supernatant of the acid-precipitated samples were collected for analysis by SDS-PAGE and Western blot.

The purification of the c2A10G6 antibody was conducted as described in (Diamos et al., 2019b). Following the purification, samples from the elutions were run on an SDS-PAGE gel to assess purity.

For the extraction of ZsE, 0.1 gram leaf samples were harvested 5 DPI and homogenized in ice-cold 1:5 w/v extraction buffer at pH 8.02 (25 mM Tris-HCl, 125 mM NaCl, 3 mM EDTA, 0.1% Triton X-100, 50 mM sodium ascorbate, and 2 mM PMSF). Homogenized leaf extracts were rotated at 4° C. for 12-15 minutes, then centrifuged at 13,000 g for 12 minutes. An uninfiltrated leaf sample was prepared using the same procedure. After centrifugation, the supernatants were collected for use in an ELISA.

Leaf tissue samples infiltrated with ZprME were harvested 4 DPI. Each leaf sample of 0.2 grams was homogenized with a 1:4 ratio w/v of PBS, pH 7.4, supplemented with 1% Triton X-100, 0.1 M sodium ascorbate, and 1 mM PMSF. An uninfiltrated sample was prepared in the same manner. The homogenized material was then centrifuged at 10,000 g for 10 minutes at room temperature. After centrifugation, the supernatant was collected for further analysis.

C. SDS-PAGE, Fluorescence Imaging, and Western Blot Analysis

Clarified extracts were mixed with SDS sample buffer (50 mM Tris-HCl, pH 6.8, 2% SDS, 10% glycerol, 0.02% bromophenol blue) under either reducing (0.5 M DTT added) or non-reducing conditions (no DTT added). Reducing samples were boiled for 10 min. Samples mixed with non-reducing buffer were not boiled but were incubated at room temperature for ~5 min after the addition of sample buffer. Samples were separated on 4-15% polyacrylamide gels (Bio-Rad, Hercules, CA) as well as stain-free 4-15% polyacrylamide gels (Bio-Rad, Hercules, CA). Florescent protein samples run under non-reducing conditions on standard 4-15% polyacrylamide gels were visualized on a UV-transilluminator and photographed for analysis. Florescent protein samples run under both reducing and non-reducing conditions on either standard or stain-free gels were analyzed using Coomassie stain (Bio-Rad, Hercules, CA, United States). A similar protocol was followed for the gels containing antibody samples. The silver stain analysis was conducted using a Pierce® Silver Stain Kit (Thermo Fisher Scientific, Waltham, MA, USA). The manufacturer's instructions were followed with a slight modification in that the gel was fixed with glutaraldehyde (12.5%) instead of 30% ethanol. All other steps were followed according to the manufacturer's protocol.

Antibody samples were electroblot transferred to PVDF membranes. PVDF membranes were blocked with 5% dry milk in PBST (PBS with 0.05% Tween-20) at 37° C. for 1 hour. Then, membranes were washed thrice with PBST before incubation with a 1:1000 dilution of goat anti-human IgG (kappa only) HRP conjugate (Southern Biotech, Birmingham, AL, USA). Bound antibody was detected with luminol reagent (Santa Cruz Biotechnologies, Santa Cruz, CA).

Samples of ZprME were electroblot transferred to PVDF membranes. PVDF membranes were blocked in 5% PBSTM overnight, washed with PBST, and probed with purified c2A10G6. After a 2-hour room temperature incubation, the membrane was washed in PBST and probed with a 1:5,000 dilution of a H1RP-conjugated goat anti-human IgG antibody (Southern Biotech, Birmingham, AL, USA). Bound antibody was detected with luminol reagent (Santa Cruz Biotechnologies, Santa Cruz, CA).

D. Plant DNA Extraction and DNA Replicon Analysis

Total plant DNA was extracted using DNeasy Plant Mini kit (Qiagen) according to the manufacturer's instructions. Purified DNA (1 µg) was digested with the indicated restriction enzymes (FIG. 3A) and run on a 1% agarose gel with ethidium bromide for DNA staining.

E. Analysis of Fluorescent Proteins

GFP and DsRed fluorescence intensity was examined on a microplate reader (Spectra Max M2, Molecular Device) at room temperature. TSP samples (25 µg) were loaded to black-wall 96-well plates (Corning) in duplicate and read with excitation and emission wavelength of 485 nm and 538 nm, respectively, for GFP, and 544 nm and 590 nm for DsRed. The fluorescence value of the negative control (extract of un-infiltrated plant leaf) was subtracted before graphing. Expression levels are reported as fluorescence units (FU) per 25 µg TSP (FIG. 3B). Fluorescence microscope images were taken using a Zeiss LSM 5 DUO (Carl Zeiss) laser scanning confocal microscope. Infiltrated leaf tissue sections were mounted with water and imaged with a Zeiss EC Plan-Neofluar 40×/1.3 oil immersion lens. Fluorescence signals for GFP, CFP, and DsRed were sequentially scanned with excitation lasers of 488, 458 and 543 nm, respectively, and detection windows of 550-560, 470-500 and 614-646 nm, respectively. For plant chlorophyll autofluorescence detection, the excitation laser of 633 nm with detection window of 630-700 nm was used. All images were taken at 512×512 pixel resolution covering an area of 318×318 µm². An 8-line average was applied to all scans with the scan speed set to 6.39 µs/pixel.

Fluorescent protein production was analyzed using ImageJ software. The band intensity of each individual protein (GFP, DsRed, CFP, and YFP) was measured and their values normalized using endogenous plant proteins to control for total protein loading.

F. ELISA Quantification of Antibody Expression Levels

A 96 well high-binding polystyrene plate (Corning Inc, Corning, NY, USA) was coated with a 1:500 dilution of unlabeled goat anti-human IgG (Southern Biotech, Birmingham, AL, USA) and incubated at 37° C. for one hour. After being washed with PBST, the plates were blocked with 5% nonfat dry milk in PBST for 30 min and washed with PBST. Multiple dilutions, ranging from 1:600 to 1:4800, of clarified plant extracts containing the different antibodies were added to the plate. Previously quantified, plant-produced antibody that was purified by protein G column chromatography was included as a standard and positive control while samples of uninfiltrated crude extract were added for a negative control. After a 1-hour incubation, the plate was washed three times in 1× PBST. Bound antibody was detected by incubating the plate with a 1:2000 dilution of goat anti-human IgG (kappa only) HRP conjugate (Southern Biotech, Birmingham, AL, USA) for 1 hour at 37° C. The plate was then washed five times with PBST, developed with TMB substrate (Thermo Fisher Scientific, Waltham, MA, USA), and the absorbance read at 450 nm.

G. ELISA Testing the Functional Characterization of cA10G6

Clarified plant extract containing the Zika soluble envelope (ZsE) was prepared as detailed above. An uninfiltrated leaf sample was also prepared in the same manner. Then, 50 L of extract was bound to a 96 well high-binding polystyrene plate (Corning Inc, Corning, NY, USA). After a one-hour incubation at 37° C., the plate was blocked with 5% PBSTM for 20 min, washed 3 times with PBST, and incubated with purified c2A10G6. After a one-hour incubation at 37° C., the bound antibody was detected by incubating the plate with a 1:2000 dilution of goat anti-human IgG (kappa only) HRP conjugate (Southern Biotech, Birmingham, AL, USA). After an hour-long incubation, the plate was washed four times in PBST, developed with TMB substrate (Thermo Fisher Scientific, Waltham, MA, USA), and the absorbance read at 450 nm.

REFERENCES

Carrington J C, Freed D D, Leinicke A J (1991) Bipartite Signal Sequence Mediates Nuclear Translocation of the Plant Potyviral NIa Protein The Plant Cell 3:953 doi: 10.2307/3869157

Chen, Q., and Davis, K. R. (2016). The potential of plants as a system for the development and production of human biologics. F1000 Research 5, 912. doi:10.12688/f1000research.8010.1.

Diamos, A. G., Crawford, J. M., and Mason, H. S. (2019a). Fine-tuning expression of begomoviral movement and nuclear shuttle proteins confers cell-to-cell movement to mastreviral replicons in Nicotiana benthamiana leaves. J. Gen. Virol. 100, 1038-1051. doi:10.1099/jgv.0.001275.

Diamos, A. G., Larios, D., Brown, L., Kilbourne, J., Kim, H. S., Saxena, D., et al. (2019b). Vaccine synergy with virus-like particle and immune complex platforms for delivery of human papillomavirus L2 antigen. Vaccine 37, 137-144. doi:10.1016/j.vaccine.2018.11.021.

Diamos, A. G., and Mason, H. S. (2018a). Chimeric 3' flanking regions strongly enhance gene expression in plants. Plant Biotechnol. J. 16, 1971-1982. doi:10.1111/pbi.12931.

Diamos, A. G., and Mason, H. S. (2018b). High-level expression and enrichment of norovirus virus-like particles in plants using modified geminiviral vectors. Protein Expr. Purif 151, 86-92. doi:10.1016/j.pep.2018.06.011.

Diamos, A. G., and Mason, H. S. (2018c). Modifying the Replication of Geminiviral Vectors Reduces Cell Death and Enhances Expression of Biopharmaceutical Proteins in Nicotiana benthamiana Leaves. Front. Plant Sci. 9, 1974. doi:10.3389/fpls.2018.01974.

Diamos, A. G., Rosenthal, S. H., and Mason, H. S. (2016). 5' and 3' Untranslated Regions Strongly Enhance Performance of Geminiviral Replicons in Nicotiana benthamiana Leaves. Front. Plant Sci. 7, 200. doi:10.3389/fpls.2016.00200.

Huang, Z., Phoolcharoen, W., Lai, H., Piensook, K., Cardineau, G., Zeitlin, L., et al. (2010). High-level rapid production of full-size monoclonal antibodies in plants by a single-vector DNA replicon system. Biotechnol. Bioeng. 106, n/a-n/a. doi:10.1002/bit.22652.

Nandi, S., Kwong, A. T., Holtz, B. R., Erwin, R. L., Marcel, S., and McDonald, K. A. (2016). Techno-economic analysis of a transient plant-based platform for monoclonal antibody production. MAbs 8, 1456-1466. doi:10.1080/19420862.2016.1227901.

We claim:

1. A geminiviral vector comprising:
   a first long intergenic region of bean yellow dwarf virus (LIR);
   a first nucleotide sequence encoding at least one transgene, wherein:
   the first nucleotide sequence further comprises at least one optimized 5' untranslated region (5' UTR) and at least one optimized 3' untranslated region (3'UTR);
   the optimized 5' UTR comprises a 35S promoter with duplicated enhancer region from cauliflower mosaic virus and at least one 5' UTR selected from the group consisting of: the psaK gene of Nicotinana benthamiana, tobacco mosaic virus, tobacco etch virus, and alfalfa mosaic virus; and
   the optimized 3' UTR comprises tobacco extension terminator with its intron removed, the 3'UTR from the ACT3 gene of N. benthamiana, and tobacco Rb7 matrix attachment region;
   a short intergenic region of bean yellow dwarf virus (SIR);
   a second LTR; and
   a second nucleotide sequence encoding the Rep/RepA of BeYDV, wherein the second nucleotide sequence is between the SIR and second LIR.

2. A geminiviral vector comprising:
   a first long intergenic region of bean yellow dwarf virus (LIR);
   a first nucleotide sequence encoding at least one transgene, wherein:
   the first nucleotide sequence further comprises at least one optimized 5' untranslated region (5' UTR) and at least one optimized 3' untranslated region (3' UTR);
   wherein the optimized 5' UTR comprises a 35S promoter with duplicated enhancer region from cauliflower mosaic virus and at least one 5' UTR selected from the group consisting of: the psaK gene of Nicotinana benthamiana, tobacco mosaic virus, tobacco etch virus, and alfalfa mosaic virus, wherein the sequence of the optimized 5' UTR has at least 99% identity to the sequence of nucleotide positions 2192-3414 of SEQ ID NO: 16, 2192-3320 of SEQ ID NO: 17, or 2192-3320 of SEQ ID NO: 18; and
   the optimized 3' UTR comprises the tobacco Rb7 matrix attachment region, and at least one member selected from the group consisting of: the tobacco extension terminator with its intron removed, the 3' UTR from ACT3 gene of N. benthamiana, the 3' UTR from pea rbcS gene, and the 3' UTR from soybean vspB gene;
   a short intergenic region of bean yellow dwarf virus (SIR);
   a second LIR; and
   a second nucleotide sequence encoding the Rep/RepA of BeYDV, wherein the second nucleotide sequence is between the SIR and second LIR.

3. A geminiviral vector comprising:
   a first long intergenic region of bean yellow dwarf virus (LIR);
   a first nucleotide sequence encoding at least one transgene, wherein:
   the first nucleotide sequence further comprises at least one optimized 5' untranslated region (5' UTR) and at least one optimized 3' untranslated region (3' UTR);
   wherein the optimized 5' UTR comprises a 35S promoter with duplicated enhancer region from cauliflower mosaic virus and at least one 5' UTR selected from the group consisting of: the psaK gene of Nicotinana benthamiana 5' UTR, tobacco mosaic virus 5' UTR, tobacco etch virus 5' UTR, and alfalfa mosaic virus 5' UTR; and
   the optimized 3' UTR comprises the tobacco Rb7 matrix attachment region, the tobacco extension terminator with its intron removed, and at least one 3' UTR selected from the group consisting of: the 3' UTR from ACT3 gene of N. benthamiana, the 3' UTR from pea rbcS gene, and the 3' UTR from soybean vspB gene, wherein at least one portion of the sequence of the optimized 3' UTR has at least 99% identity to the sequence of nucleotide positions 4345-5317 of SEQ ID NO: 16, 7119-9536 of SEQ ID NO: 16, 4219-5735 of SEQ ID NO: 17, 5984-6632 of SEQ ID NO: 17, 3414-3714 of SEQ ID NO: 18, or 4345-5523 of SEQ ID NO: 18;

a short intergenic region of bean yellow dwarf virus (SIR);

a second LIR; and a second nucleotide sequence encoding the Rep/RepA of BeYDV, wherein the second nucleotide sequence is between the SIR and second LIR.

4. The geminiviral vector of claim 2, wherein the vector is the vector backbone pBYKEHM-Bsa (SEQ ID NO: 18), pBYKEAM-BAGFPas6H (SEQ ID NO: 17), or pBY11 HA-GFP (SEQ ID NO: 16).

5. The geminiviral vector of claim 2, wherein the vector comprises a portion with at least 99% sequence identity to the sequence of nucleotide positions 1-3424 of SEQ ID NO: 16, 17 and 18; and a portion with at least 99% sequence identity to the sequence of nucleotide positions 4247-14211 of SEQ ID NO: 17 and 18 or 1707-17111 of SEQ ID NO: 16.

6. The geminiviral vector of claim 3, wherein the vector is the vector backbone of pBYKEHM-Bsa, pBYKEAM-BAGFPas6H, or pBY11 HA-GFP.

7. The geminiviral vector of claim 3, wherein the vector comprises:

a portion with at least 99% sequence identity to the sequence of nucleotide positions 1-3424 of SEQ ID NO: 16, 17 and 18; and a portion with at least 99% sequence identity to the sequence of nucleotide positions 4247-14211 of SEQ ID NO: 17 and 18 or 7107-17111 of SEQ ID NO: 16.

* * * * *